US010766029B2

(12) United States Patent
Cox

(10) Patent No.: US 10,766,029 B2
(45) Date of Patent: Sep. 8, 2020

(54) DEVICE, PLATFORM, AND ASSAY FOR ASSESSING CELLS

(71) Applicant: CELLS FOR CELLS S.A., Las Condes (CL)

(72) Inventor: Juan Pablo Acevedo Cox, Santiago (CL)

(73) Assignee: CELLS FOR CELLS S.A., Las Condes (CL)

(*) Notice: Subject to any disclaimer, the term of this patent is extended or adjusted under 35 U.S.C. 154(b) by 128 days.

(21) Appl. No.: 15/551,007

(22) PCT Filed: Feb. 22, 2016

(86) PCT No.: PCT/IB2016/000274
§ 371 (c)(1),
(2) Date: Aug. 14, 2017

(87) PCT Pub. No.: WO2016/132221
PCT Pub. Date: Aug. 25, 2016

(65) Prior Publication Data
US 2018/0236442 A1    Aug. 23, 2018

(30) Foreign Application Priority Data

Feb. 20, 2015 (WO) .................. PCT/IB2015/051317

(51) Int. Cl.
B01L 3/00      (2006.01)
G01N 33/50     (2006.01)

(52) U.S. Cl.
CPC ........... B01L 3/5025 (2013.01); B01L 3/5027 (2013.01); G01N 33/5008 (2013.01);
(Continued)

(58) Field of Classification Search
CPC ............ B01L 3/5025; B01L 3/5027; B01L 2200/0694; B01L 2300/069;
(Continued)

(56) References Cited

U.S. PATENT DOCUMENTS 5,637,469 A        6/1997  Wilding et al.
2002/0168757 A1*  11/2002  Kirk ................... B01L 3/5025
                                                       435/288.5

(Continued)

FOREIGN PATENT DOCUMENTS

WO    2014/042463 A1    3/2014

OTHER PUBLICATIONS

Marui et al. "Simultaneous application of basic fibroblast growth factor and hepatocyte growth factor to enhance the blood vessels formation" Jan. 2005, Journal of Vascular Surgery, 41, 1, 82-90 (Year: 2005).*

(Continued)

Primary Examiner — Matthew D Krcha
Assistant Examiner — Quocan B Vo
(74) Attorney, Agent, or Firm — Merchant & Gould P.C.

(57) ABSTRACT

Devices are for assessing the migration response in the presence of a stable encapsulated gradient of a factor or factor combination, and quantifying the adherence response inside micro-channels in the presence of different factors. A platform is for obtaining information relating to migration score or the quantification of adhered cells through use of the devices, and it allows this information to be used to assess therapeutic potential. A method quantifies the cells migration response and the cell adherence response.

21 Claims, 30 Drawing Sheets

(52) U.S. Cl.
CPC .. *G01N 33/5029* (2013.01); *B01L 2200/0694* (2013.01); *B01L 2300/069* (2013.01); *B01L 2300/0816* (2013.01); *B01L 2300/0864* (2013.01); *B01L 2400/0409* (2013.01)

(58) Field of Classification Search
CPC ..... B01L 2300/0816; B01L 2300/0864; B01L 2400/0409; G01N 33/5008; G01N 33/5029
See application file for complete search history.

(56) References Cited

U.S. PATENT DOCUMENTS

| | | | |
|---|---|---|---|
| 2006/0083773 A1* | 4/2006 | Myung | A61F 2/142 424/427 |
| 2006/0160066 A1 | 7/2006 | Bhatia et al. | |
| 2009/0136982 A1 | 5/2009 | Tang et al. | |
| 2011/0117579 A1 | 5/2011 | Irimia | |
| 2011/0159522 A1* | 6/2011 | Kamm | C12Q 1/02 435/7.21 |
| 2014/0057311 A1* | 2/2014 | Kamm | B01L 3/502753 435/29 |
| 2015/0018226 A1 | 1/2015 | Hansen et al. | |

OTHER PUBLICATIONS

Sundararaghavan et al. "Neurite Growth in 3D Collagen Gels With Gradients of Mechanical Properties" Biotechnology and Bioengineering, Aug. 8, 2008, p. 632-643 (Year: 2008).*

Goyal et al. "Neuronal Micro-culture Engineering by Microchannel Devices of Cellular Scale Dimensions" Apr. 29, 2011, Biomedical Engineering Letters,1, 2, 89-98 (Year: 2011).*

Tan et al. "Cloning and characterizing mutated human stromal cell-derived factor-1 (SDF-1): C-terminal α-helix of SDF-1α plays a critical role in CXCR4 activation and signaling, but not in CXCR4 binding affinity" Nov. 2006, Experimental Hematology,34, 11, 1553-1562 (Year: 2006).*

Holland et al. "Dual growth factor delivery from degradable oligo(poly(ethylene glycol) fumarate) hydrogel scaffolds for cartilage tissue engineering" Aug. 14, 2004, Journal of Controlled Release, 101, 11-125 (Year: 2020).*

Guangwei Si et al: "A parallel diffusion-based microfluidic device for bacterial chemotaxis analysis", Lab on a Chip, vol. 12, No. 7, Jan. 1, 2012 (Jan. 1, 2012), pp. 1389 (Year: 2012).*

Wong et al: "Partitioning microfluidic channels with hydrogel to construct tunable 3-D cellular microenvironnnents", Biomaterials, Elsevier Science Publishers BV., Barking, GB, vol. 29, No. 12, Feb. 19, 2008 (Feb. 19, 2008), pp. 1853-1861 (Year: 2008).*

Haessler et al. "Dendritic cell chemotaxis in 3D under defined chemokine gradients reveals differential response to ligands CCL21 and CCL19" Apr. 2011, PNAS 108, 14 5614-5619 (Year: 2011).*

International Search Report and Written Opinion for International Application No. PCT/IB2016/000274, dated Aug. 16, 2016, 12 pages.

Annabi, N. et al., "Hydrogel-coated microfluidic channels for cardiomyocyte culture," Lab on a Chip, 2013, vol. 13, pp. 3569-3577.

* cited by examiner

Table 1: Melting characterization of gelatin solutions (7%).

|  | Salmon Gelatin | | Bovine Gelatin | |
|---|---|---|---|---|
|  | Non Methacrylated | Methacrylated | Non Methacrylated | Methacrylated |
| Tm (°C) | 4.26 (±0.026) | 4.09 (±0.080) | 12.20 (±0.008) | 9.69 (±0.198) |
| ΔH (J/g) | 0.88 (±0.028) | 0.48 (±0.088) | 1.20 (±0.016) | 0.73 (±0.010) |
| ΔT (°C) | 11.19 (±0.020) | 10.97 (±0.143) | 19.72 (±0.013) | 17.46 (±0.163) |

Results are shown as average (± standard deviation).

A

Cell Loading Wall

Migration lanes

Hydrogel walls

B

Encapsulated factor    Released factor

A

B

C

D

E

F

G

Scratch Assay (12 hr)

MSCs (BM) + VEGF (10 ng/ml)

MSCs (BM) + VEGF (10 ng/ml) + 2.5 U/ml

A c
- Device elements:
- Release of a stable gradient of factors to direct cell migration Subpopulation 1:

Subpopulation 2:

Subpopulation 1

Subpopulation 2

DEVICE, PLATFORM, AND ASSAY FOR ASSESSING CELLS

CROSS REFERENCE TO RELATED APPLICATIONS

This application is a National Stage Application of PCT/IB2016/000274, filed Feb. 22, 2016, which claims priority to PCT/IB2015/051317, filed Feb. 20, 2015, the contents of which are incorporated herein by reference in their entirety. To the extent appropriate, a claim of priority is made to each of the above disclosed applications.

TECHNICAL FIELD

This invention relates to a cell-based assay, platform, and device for high-throughput quantification of directed cell migration, and assessing cell migration response. Another aspect of the invention relates to a device for measuring cell adherence response. Such devices and platforms are useful for assessing the therapeutic potential of cells and can be applied in cell therapy, cancer research, diagnostics, drug discovery, cell migration, angiogenesis, embryogenesis, axon growth, immunology, amongst many others.

BACKGROUND

Current potency or therapeutic quality tests of cell products used in the cellular therapy area, including simple cellular feasibility tests (live or dead cells) and metabolic activity (amount of ATP), provide very little information related to therapeutic effects in front of pathologies. Some companies have developed potency tests based on the recognition of cell surface markers or through ELISA tests (Enzyme-Linked ImmunoSorbent Assay), which have demonstrated certain success in particular cases; however, because these current tests assess just one or a few biologic activities, predictive power with regard to the therapeutic effect may be considered relatively low. This is mainly due to the fact that specific biologic activity relevance could be cancelled in the event other biologic activities are low or non-existing. The results of including this type of potency test are quite variable cellular products or doses, which implies a varied therapeutic efficiency and, therefore, a poor standardization of cell therapies. The FDA understood the issues related to potency tests for cellular products and generated a guide for the sector industry in 2012, which evidences the importance of developing quick potency tests capable of assessing multiple biologic activities, and that are designed and independently validated for different types of pathologies. The evident deficiencies of current potency tests partly explain the poor success of clinical studies, and also the regulating entities', such as the FDA's reluctance regarding the use of adult stem cells in patients.

In cell therapy, the therapeutic efficacy of cells is affected by a myriad of elements that influence their final therapeutic potency, which are still not fully understood. These elements may include donor-related elements such as the genetic background, age, health conditions, habits, etc., and process-related effects such as culture conditions, level of cell expansion, cryopreservation and dose preparation. All of these elements play a role in assessing the final product, specifically at the therapeutic level. In order to maintain the quality of therapeutic products, similarly to pharmaceutical drugs, cell products need to be tested for safety, identity, purity, and potency. However, unlike pharmaceutical drugs, the therapeutic effect of cells is based on the orchestration of multiple biological activities, while for drugs are based on the known mechanism of an individual active compound.

Due to the high heterogeneity of cell productions, and the costly and time-consuming process of quality verification, a quick potency test capable to control the therapeutic quality of cellular doses for a particular treatment has become an outstanding need in the field of cellular therapy. In vitro quick tests and testing devices could accelerate and make more efficient the steps of cell donor recruitment, manufacturing control, lot release, and the testing of cellular doses before therapeutic injection into patients.

SUMMARY

Provided herein are cell-based assays, platforms, and devices useful for assessing the therapeutic potential of cells, which can be applied in cell therapy, cancer research, diagnostics, drug discovery, cell migration, angiogenesis, embryogenesis, axon growth, immunology, amongst many others. Such assays, platforms, and devices as described herein provide for high-throughput quantification of directed cell migration, assessing cell migration response, and cell adherence responses in populations of cells.

Another aspect of the invention relates to a device for measuring cell adherence response. This device quantifies a directed adherence response trigger by the presence of migration-inducing factors. While not wishing to be limited by theory, mechanistically, adult stem cells or immune cells in the blood stream can respond to those factors by first activating the formation of cell adhesions complexes. The cells stop flowing and later they transmigrate into tissue. One of the advantages of this device is that it can assess a cell response that happens shortly after sensing the factor, which means the assessment can be done within minutes after factor exposure.

One aspect of the invention provides devices capable of assessing the migration response in the presence of a stable encapsulated gradient of a factor or factor combination inside micro-channels in the presence of different factors. In some embodiments, the device for measuring cell adherence response does not include a gradient.

Another aspect of the invention provides a platform for the obtained information thanks to the devices, and it allows obtaining already the migration score or the quantification of adhered cells.

In one embodiment of this invention, a device is provided capable of assessing the migration response in the presence of a stable encapsulated gradient of a factor or factor combination, particularly for cells used to treat certain pathology. Quantification of the cells migratory response to the defined factor is correlated to a given therapeutic quality level, and it is an information source on the cell sample general performance and therapeutic quality. According to this invention, the device includes a stable gradient encapsulated in hydro-gels forming physically delimited migration paths. Gradients and geometric restriction to a traffic dimension amplify cell migration response and facilitate reading and analyzing the device. Migration values and factor identity are included in a statistics mathematical model to note or predict the stem cells therapeutic or potential quality in front or given pathologies.

In a second embodiment of this invention, a device is provided to quantify adherence response in micro-channels in front of different factors presence. The adherence response is recognized as a key element for good therapeutic results of cell products.

In another embodiment of this invention, a therapeutic potency predicting device or kit for cell products is provided. As with the first device, the factor adherence and identity values, according to this invention second realization, are included in a statistics mathematical model that allows noting or predicting the stem cells therapeutic or potential quality in front of certain pathologies. The main difference compared to the first device is the fact that this provides quicker results, and its application is best indicated for cases where results are required in a shorter time, as in the testing of cell products therapeutic quality just before their administration to patients.

Another aspect of the invention is related to the field of adult stem cells isolated from different tissues, as well as of embryonic origin. Particularly, the invention is focused on the assessment and quantification of the potential or therapeutic quality of a stem cell sample before its storage in cell banks before their clinical or therapeutic use in patients and for the control of therapeutic quality in the different manufacturing stages of a product resulting from stem cells, which also includes donor recruitment, and also as criteria for the release of production batches to the market. Moreover, the device can be used in any research field that involves migration or adherence response.

According to this invention, the therapeutic potential quantification allows a quick and quality assessment of stem cells according to the cell adherence to substrate response and migration in the presence of a particular factor gradient. In general terms, the different factors included in the invention allow the assessment of multiple biologic activities finally translated into a migration or adherence cell response which, after being included, provide a predictive value of the therapeutic efficiency on specific pathologies. The invention serves as a tool capable of standardizing the production of cell doses with a given quality.

Quantification of the cellular response in front of a given factor occurs with the support of a method and/or a technology platform. This platform is capable of co-relating multiple responses from multiple factors with a therapeutic quality level, which provides a source of information on the cellular preparation general response.

Accordingly, one aspect of the invention relates to a device to for analyzing a population of cells, the device comprising: a) a cell load chamber; b) at least two parallel assay lanes or lines spaced at an equal distance from each other; each assay lane or line comprising a hydro-gel; and c) at least two parallel assay channels.

In some embodiments, the cell load chamber is removable or not removable.

In some embodiments, the device comprises at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty assay lanes or lines. In some embodiments, the device comprises sixteen assay lanes or lines.

In some embodiments, the assay lanes or lines comprise a width of about 1 µm, 2 µm, 3 µm, 4 µm, 5 µm, 6 µm, 7 µm, 8 µm, 9 µm, 10 µm, 12 µm, 14 µm, 16 µm, 18 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 1050 µm, 1100 µm, 115 µm, 120 µm, 125 µm, 130 µm, 1350 µm, 140 µm, 145 µm, 150 µm, 155 µm, 160 µm, 165 µm, 170 µm, 175 µm, 180 µm, 185 µm, 190 µm, 195 µm, or 120 µm. In some embodiments, the width of the assay lines or lanes is about 150 µm.

In some embodiments, the device comprises at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty assay channels. In some embodiments, the device comprises fifteen assay channels.

In some embodiments, the assay lanes or lines are spaced at a distance apart to form at least one assay channel.

In some embodiments, the assay lanes or lines are spaced at a distance apart to form at least 5, 10, 15, 20, 25, 30, 35, or more assay channels. In some embodiments, the device comprise 15 assay channels.

In some embodiments, the assay channel comprise a width of about 1 µm, 2 µm, 3 µm, 4 µm, 5 µm, 6 µm, 7 µm, 8 µm, 9 µm, 10 µm, 12 µm, 14 µm, 16 µm, 18 µm, 20 µm, 22 µm, 24 µm, 26 µm, 28 µm, 30 µm, 32 µm, 34 µm, 36 µm, 38 µm, 40 µm, 42 µm, 44 µm, 46 µm, 48 µm, 50 µm, 55 µm, 60 µm, 65 µm, 70 µm, 75 µm, 80 µm, 85 µm, 90 µm, 95 µm, or 100 µm. In some embodiments, the assay channel width is about 50 µm.

In some embodiments, the assay channel comprises a height of about 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, or 100 µm. In some embodiments, the assay channel height is about 50 µm.

In some embodiments, the assay channel comprise a length of about 1 mm, 2 mm, 3 mm, 4 mm, 5 mm, 6 mm, 7 mm, 8 mm, 9 mm, 10 mm, 12 mm, 14 mm, 16 mm, 18 mm, 20 mm, 22 mm, 24 mm, 26 mm, 28 mm, 30 mm, 32 mm, 34 mm, 36 mm, 38 mm, 40 mm, 42 mm, 44 mm, 46 mm, 48 mm, or 50 mm. In some embodiments, the assay channel length is about 10 mm.

In some embodiments, the hydro-gel is characterized by a encapsulated factor gradient comprising a range of higher to lower concentrations of at least one migration or adherence inducing factor.

In some embodiments, the hydro-gel comprises at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty migration or adherence inducing factor.

In some embodiments, the migration or adherence inducing factor is selected from the group consisting of Thrombin (F2), Interleukin 8 (IL-8, CXCL8), Factor derivative from 1α (SDF-1α, CXCL12) cell stroma, Wnt11, Wnt3, Leptin (LEP), Interleukin-13 (IL-13), Angiotensin II (ANGII), Melanoma cell adherence molecule (MCAM, CD146), Interleukin 2 (IL-2), Fibroblast growth factor 1 (FGF-1), Fibroblast growth factor 2 (FGF-2), Low molecular weight hyaluronic acid (LMWHA), Beta transforming growth factor (TGF-beta), Vascular endothelial growth factor (VEGF-B and VEGF-A), Lysophosphatidic acid, Regulated upon Activation, Normal T-cell Expressed, and Secreted (RANTES, CCL5), Interferon gamma-induced protein 10 (CXCL10, IP-10), Monocyte 1 chemoattractant protein 1 (MCP1, CCL2), Macrophage inflammatory protein 1α (MIP1α, CCL3), Macrophage inflammatory protein-1β (MIP-1β, CCL4), Chemokine (C—C motif) ligand 7 (CCL7), Macrophage inflammatory protein-3-beta (MIP-3-beta, CCL19), Chemokine (C—C motif) ligand 21 (CCL21), Chemokine (C—C motif) ligand 25CCL25, Lymphocyte B chemoattractant B (CXCL13), Chemokine (C—X—C motif) ligand 16 (CXCL16), Tumor necrosis factor-α (TNF-α), Hepatocytes growth factor (HGF), Epidermal growth factor (EGF), Platelet derivative growth factor (PDGF), Insulin growth factor (IGF), Angiopoietin-1 (AN-GPT1), and Granulocyte colony stimulating factor (G-CSF), or combinations thereof.

In some embodiments, the encapsulated factor gradient comprises a concentration range of migration or adherence inducing factor from about 1 nM to 400 nM.

In some embodiments, the concentration of migration or adherence inducing factor is about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 125 nM, 150 nM, 175 nM, 200 nM, 225 nM, 250 nM, 275 nM, 300 nM, 325 nM, 350 nM, 375 nM, or 400 nM.

In some embodiments, the encapsulating factor gradient is release upon addition of a release factor.

In some embodiments, the release factor is a protease.

In some embodiments, the protease is a collagenase.

In some embodiments, the cells are selected from the group consisting of mesenchymal stem cells, early mesenchymal/stromal precursor cells, adipose tissue-derived stem cells, Muse-AT cells, hematopoietic cells, hematopoietic stem cells, platelets, Kupffer cells, osteoclasts, megakaryocytes, granulocytes, NK cells, endothelial precursor or progenitor cells, pluripotent cells, CD34+ cells, Stro-1+ cells, Stro-3+ cells, CD29+ cells, CD166+ cells, Thy-1+ or CD90+ stem cells, CD44+ cells, immune cells, monocytes, leukocytes, lymphocytes, B and T cells, NK cells, macrophages, neutrophil leukocytes, neutrophils, neutrophil granulocytes, adult and embryo stem cells, endoderm mesenchymal stem cells (MSCs), mesoderm MSC, ectoderm MSC, early mesenchymal/stromal precursor, adipose tissue-derived stromal/stem cells, multipotent stem cells, adipocytes, osteocytes, chondrocytes, myoblasts, cardiomiocytes, astrocytes, and neuronal/glial cell lineages.

In some embodiments, the hydro-gel comprises gelatin, hyaluronic acid, alginate, agarose, chitose, gellan gum, collagen, collagen based hydrogel, high methacrylated salmon gelatin at 10%, polyethylene glycol, polyethylene acid, polyvynylpirrolidone, polyacrylamide, polymetyl methacrylate, polyethylene glycol dyacrilate based formula (PEGDA), pentaerythritol triacrylate (PETA), acrylic acid, acrylamide, or combinations thereof.

In some embodiments, the hydro-gel comprises collagen based hydrogel. In some embodiments, the hydro-gel further comprises a photo initiator. In some embodiments, the photo initiator comprises 2-hydroxy-4'-(2-hydroxyethoxy)-2-methylpropiophenone or 2.2-dimethoxy-2-phenyl acetophenone. In some embodiments, the hydro-gel is provided in a non-polymerized form. In some embodiments, the hydro-gel is polymerized upon exposure to UV light.

Another aspect of the invention relates to a device set forth herein which is adapted to assess cell migration response of a population of cells.

Another aspect of the invention relates to a device set forth herein adapted to assess cell adherence response of a population of cells, the device comprising:
  a) a micro-channel circuit for the perfusion of a liquid medium;
  b) an internal substrate limiting channel edges;
  c) at least one entry for a liquid medium injection; and
  d) at least one entry for a sample cells.

In some embodiments, the micro-channel circuit optionally contains certain adherence inducing factors.

In some embodiments, the internal substrate optionally contains a coverage.

In some embodiments, the coverage facilitates the cell adherence and/or presents or releases adherence inducing factors.

In some embodiments, incorporates a main element in the hydro-gel, which could be another hydro-gel or material in order to increase the construct structural stability.

In some embodiments, the release or presentation of factors could occur from hydro-gels in a unit separated from the unit where cells are migrating, and mounted or coupled in a way to allow the factors gradient be recognized by the cells.

In some embodiments, includes a factor gradient into the device.

In some embodiments, the formation of the gradient could be defined by a factor release unit formed by a hydro-gel or other material and is positioned in one of the channel or migration line ends.

In some embodiments, the gradient elements and the physical restriction in migration lanes or lines in the device could be defined by exclusive cell adherence areas, with no need to include hydro-gels or other materials that limit cell lateral mobility.

In some embodiments, the exclusive cell adherence areas are made through patterns defined by adsorption or covalent binding.

In some embodiments, the exclusive cell adherence areas include growing factor gradients inducing migration.

Another aspect of the invention relates to a method to quantify the cells migration response of a population of cells, the method comprising the steps of:
  a) providing the cells to the device according to any one of the preceding claims;
  b) incubating the cells under appropriate conditions to facilitate migration;
  c) calculating the migration distance of cells contained in the sample to generate at least one score;
  d) incorporating the at least one score in a statistical mathematical model specific to a cell type and pathology;
  e) obtaining a correlation between the factor defined and the therapeutic quality level; and
  f) calculating a general performance value and the therapeutic quality of the cell sample.

Another aspect of the invention relates to a method to quantify the cells adherence response, the method comprising the steps of:
  a) calculating the number of cells withheld in the channel circuit;
  b) including the values in a statistics mathematical model specific to the cell type and pathology;
  c) obtaining a correlation between the factor defined and the therapeutic quality level; and
  d) calculating a general performance value and the therapeutic quality of the cell sample.

Another aspect of the invention relates to use of the device set forth herein characterized in that it is used to assess therapeutic characteristics of a sample stored in a cell bank.

In some embodiments, the use is characterized in that it serves as quality control before therapy and after thawing a cell sample.

In some embodiments, the use is characterized in that it is used to assess cell migration or adherence in the presence of factors that could be related to the rate of success in different treatments, such as kidney damage recovery or other pathologies.

In some embodiments, the use is characterized in that it is used to calculate the therapeutic variability of a cell sample or product according to the cells activity in the devices.

In some embodiments, the use is characterized in that it is used to calculate the cells doses to be administered to a patient when treating certain pathology.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Panel B shows factors release or presentation could be from hydro-gels in a unit separate from the unit where cells are migrating, and mounted or coupled in a way to allow factor gradient recognition by the cells, where (a) corresponds to hydro-gel or other material for factor controlled release, (b) corresponds to polystyrene, glass, or other material for cell migration support and (c) corresponds to hydro-gel or other material for structural support. Panel C shows an alternative, forming of the gradient could be defined by a factor release unit formed by a hydro-gel or other material positioned in one of the channels or migration lines' ends, where (a) corresponds to the factor released gradient, (b) corresponds to the hydro-gel or other material for factor controlled release, and (c) corresponds to the hydro-gel or other material for structural support.

Figure 4:
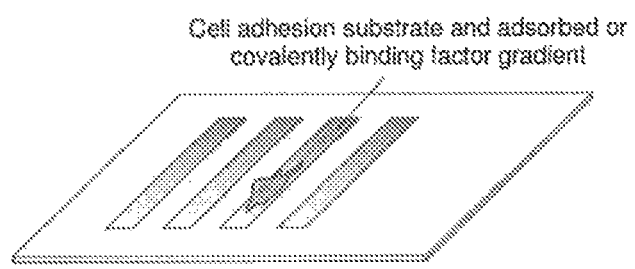

FIG. 4 shows inside the device, gradient elements and physical restriction of the migration lines or lanes may be defined as exclusive areas of cellular adherence, with no need to include hydro-gels or other materials limiting the cells lateral mobility.

Figure 5:
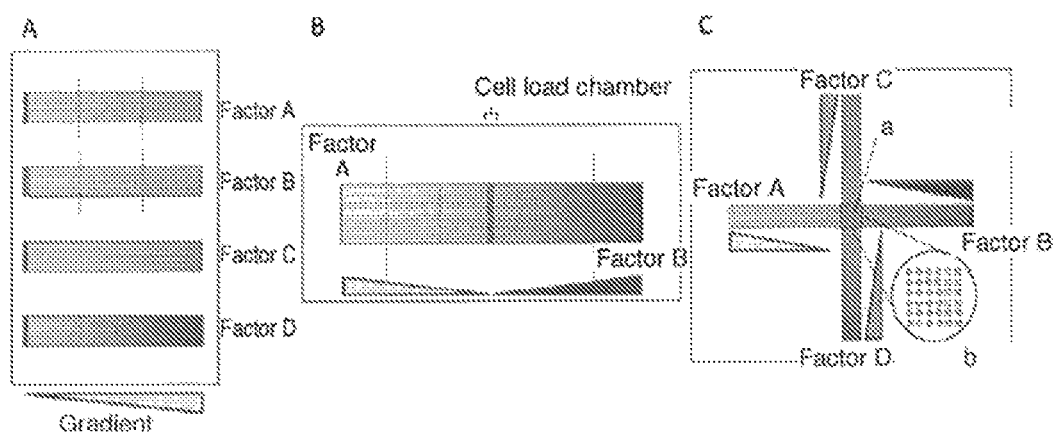

FIG. 5 shows that the devices may include the use of different migration inducing factors and in different designs, some of them examples in this figure, which may be used for different applications, where A shows the Cell load chamber, B shows the Load chamber bottom, and C shows an embodiemnt with four factor gradients.

Figure 6:
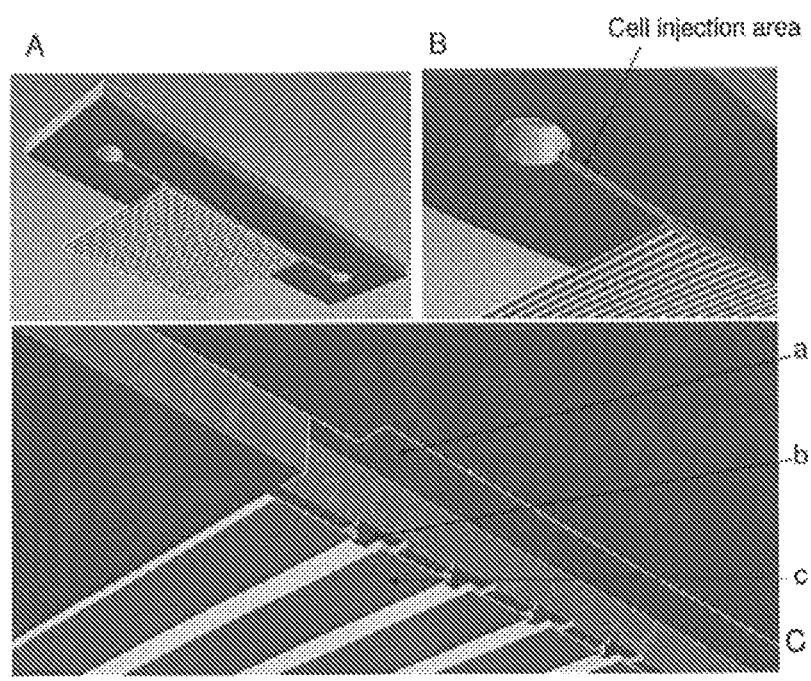

FIG. 6 shows a non-removable load chamber. Some load chambers may be removed after the cells adherence to the substrate in order to allow their migration to the migration channels. This figure shows a non-removable load chamber design, where small spaces 10 um high are aligned to spaces between hydro-gels forming the migration lines. These 10 um high spaces connect the space where cells are entered and the migration area. Spaces must be small enough to prevent the cells from passing to a non-adhered condition, but they should be able to cross them once adhered to the substrate. Where A. shows a view from the lower part, where the surface to which cells adhere was left transparent; B. shows the cell injection area; and C. shows (a) the Lower view of cell deposit chamber, (b) shows Cell passing channel and (c) shows Hydro-gels with encapsulated factors.

Figure 7:
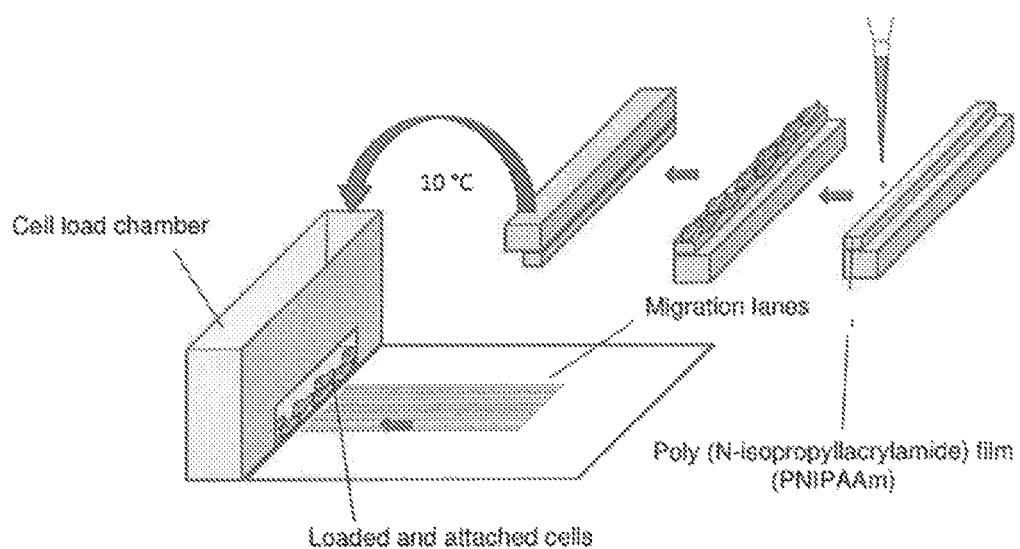

FIG. 7 shows a removable load chamber alternative includes the use of cell adherence substrates that respond to temperature. Examples are the PNIPAAm films which, at 37° C. temperature, appear in hydro-phobic condition and allow cell adherence. At temperatures below 30° C., this film becomes hydro-phobic and causes swelling due to water absorption and cells lose their adherence. This way, it is possible to transfer cell lines adhered to the device migration area beginning.

Figure 8:
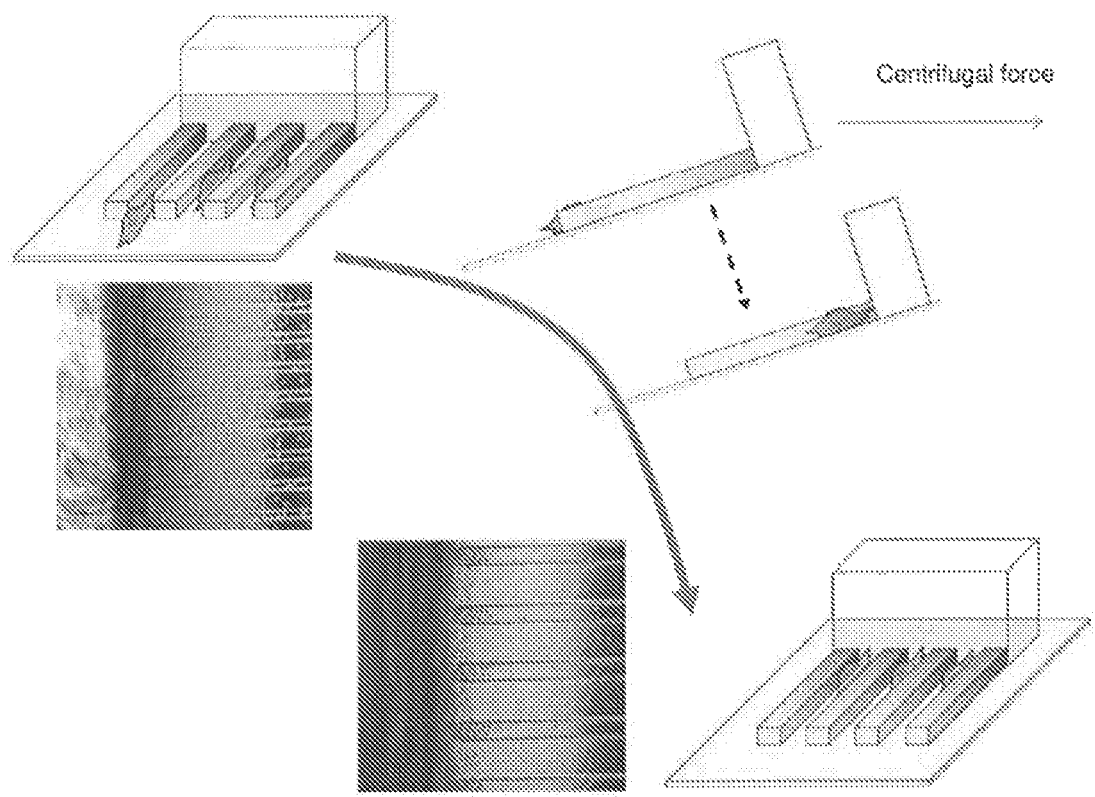

FIG. 8 shows another non-removable cellular load chamber includes locating the cells at the beginning of migration lanes by centrifuging at an angle between 190-230° with regard to the device plane. Besides, it is necessary to consider a physical barrier at the lanes beginning in order to stop the cells forced displacement induced by the centrifuging force. Then, it is possible to observe how the homogeneous distribution in the device field becomes a localized distribution at the migration channels beginning.

Figure 9:
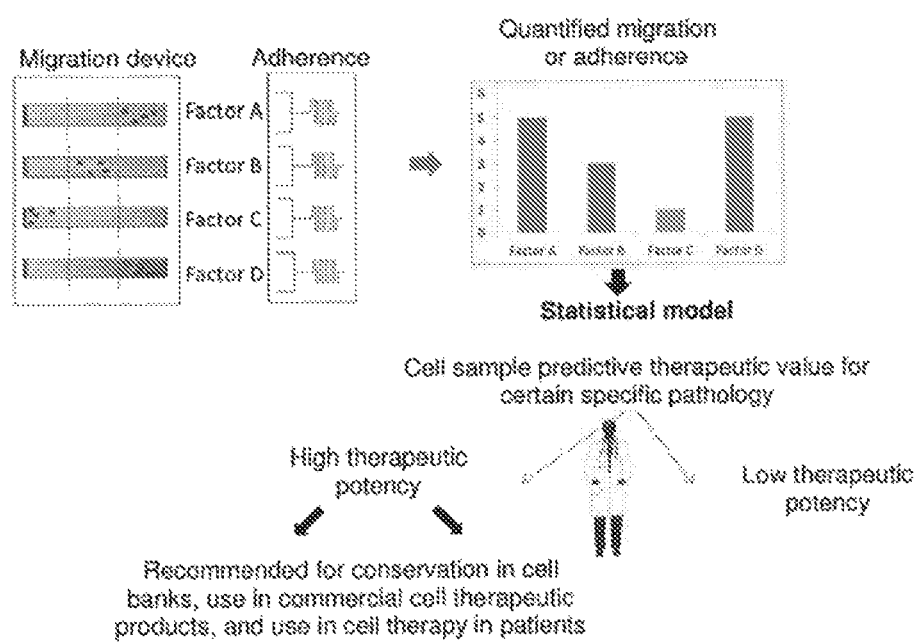

FIG. 9 shows a device operation based on migration assessment, and device based on adherence assessment. Device Operation as Therapeutic Potency Test. Each device contains a list of previously selected factors identified as relevant when correlating cells response in front of these factors and therapeutic potential in front of certain diseases. After quantifying migration and/or adherence, values are included to a mathematical model that may additionally be fed by the quantification of the expression of certain proteins by the cell sample. The mathematical model will provide a therapeutic potency predictive correlated value of the tested cell sample.

Figure 10:
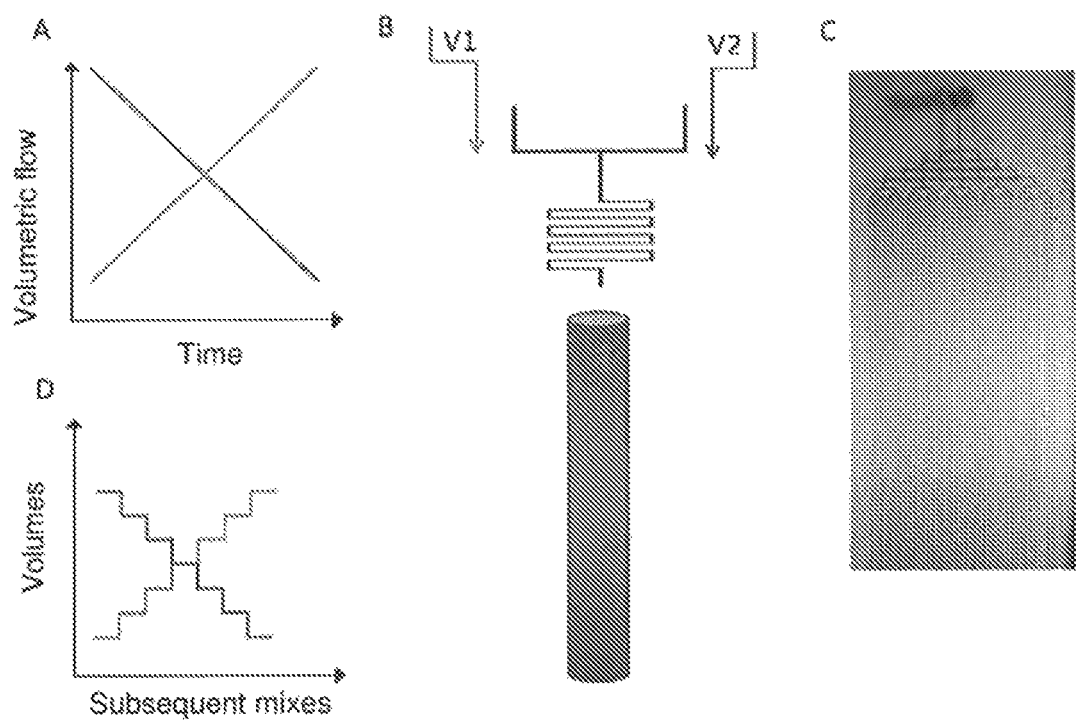

FIG. 10 shows forming of a series of parallel hydro-gels that encapsulate a certain factor gradient. Section A shows a graph of volumetric flow versus time and a graph of volume versus subsequent mixes. Section B shows a diagrammatic view of flows. According to the flow distribution design in the micro-channel circuit in Section C, a gradient orderly entry to this system would allow its distribution in parallel channels. After stopping the gradient flow, the non-polymerized hydro-gel solution is polymerized in order to encapsulate the gradient inside the hydro-gel. Before its inclusion in the micro-channel circuit, the gradient may be formed using different methodologies. In this invention, this gradient may be created by mixing two flows variable in time, one containing a certain factor concentration and the second one without factor, as indicated in part A in the figure, where both converge into a single channel that later results in the forming of a micro-channels set, as observed in part C in the same figure. Alternatively, the gradient may be formed by growing discreet concentration mixes of the factor (part D), which are included one by one into a series inside the distribution channels. To the extension these growing concentrations of each mix included in the distribution channels are less differentiated, the final gradient result in the device will be more lineal.

Figure 11:
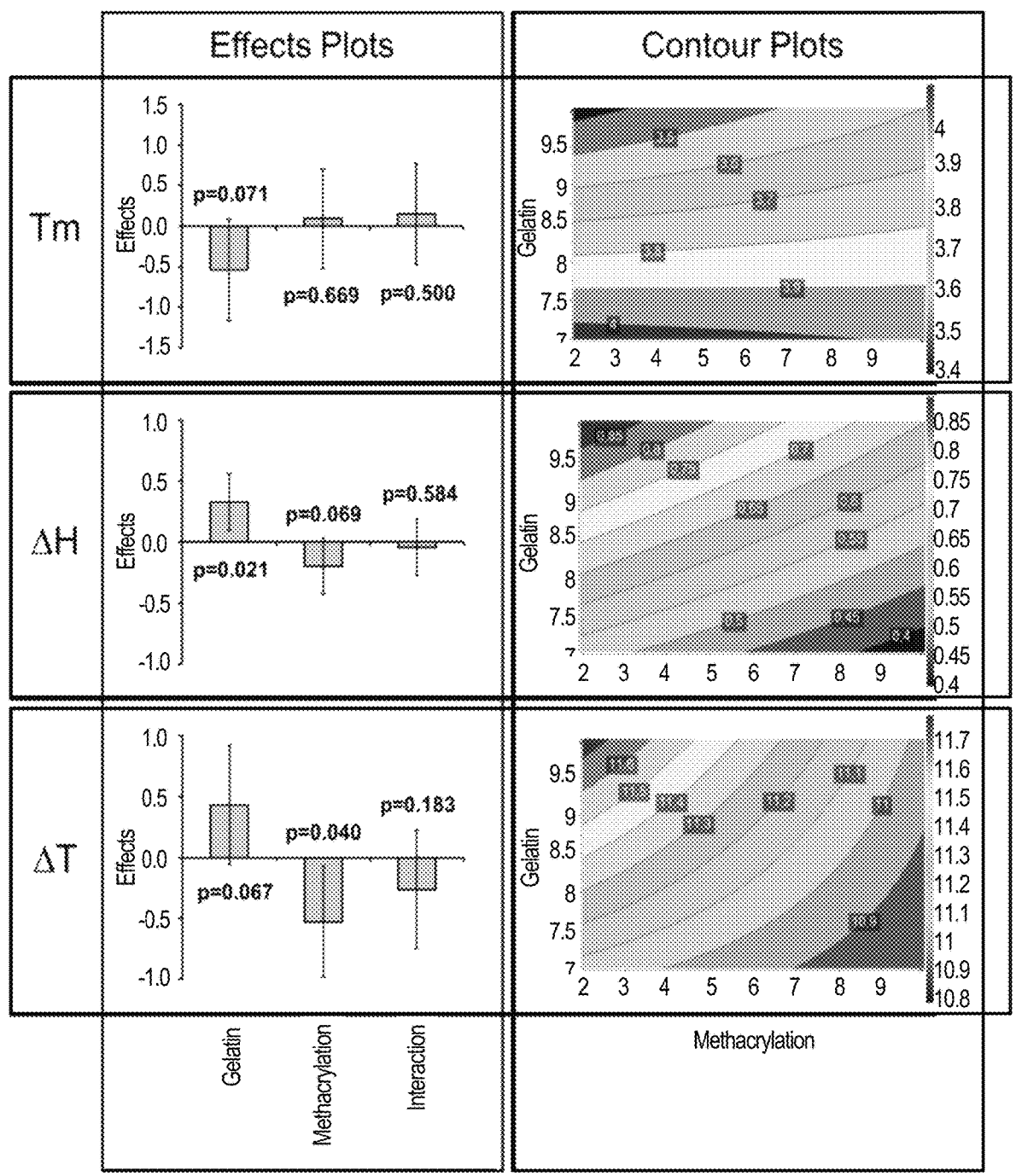

FIG. 11 includes two parts, A and B. A shows the effects and contour plots in enthalpy change ($\Delta H$), temperature difference ($\Delta T$), and melting temperature (Tm) of different hydro-gel materials based on the type of material (salmon or bovine gelatin) and the levels of chemical functionalization (high or low), described as methacrylation, which is covalent addition of methacryloyl groups in the material monomers. B shows the melting data of materials used in the hydro-gel, including enthalpy change ($\Delta H$), temperature difference ($\Delta T$), and melting temperature (Tm). The data compare materials based on salmon and bovine gelatin, and with or without presence of methacryloyl groups in the monomer chain.

Figure 12:
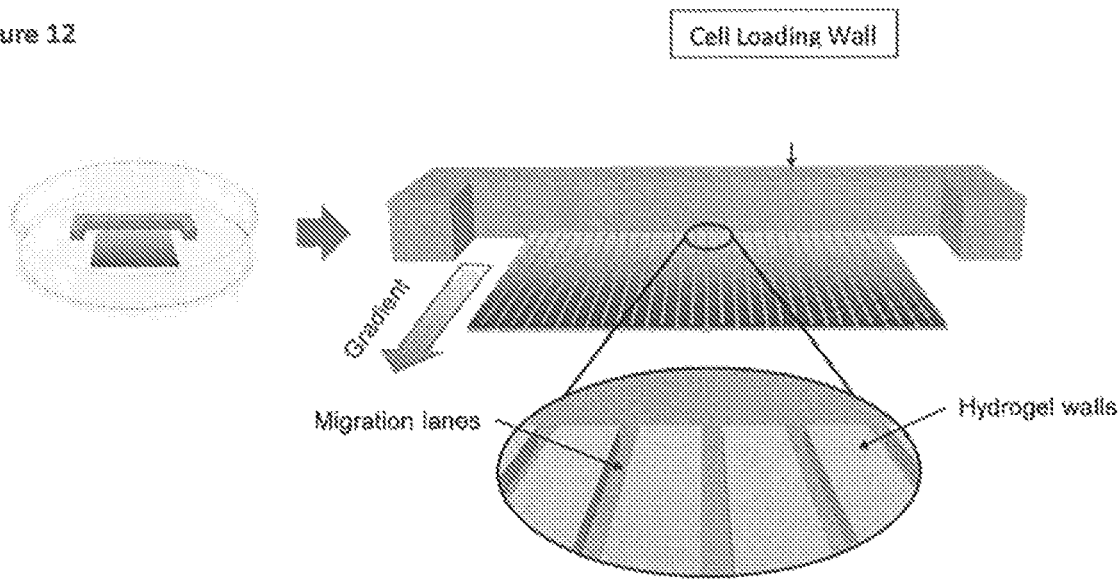
Figure 12:
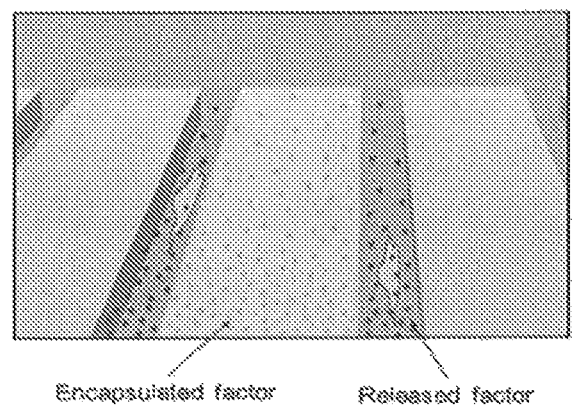

FIG. 12 shows an exemplary example of the device, with cell loading wall, migration lanes, and hydrogel walls in between migration lanes in section A of the Figure. The encapsulated gradient of migration-inducing factors is as well exemplified and the release of factors into the migration lanes is shown in the section B of the figure.

Figure 13:
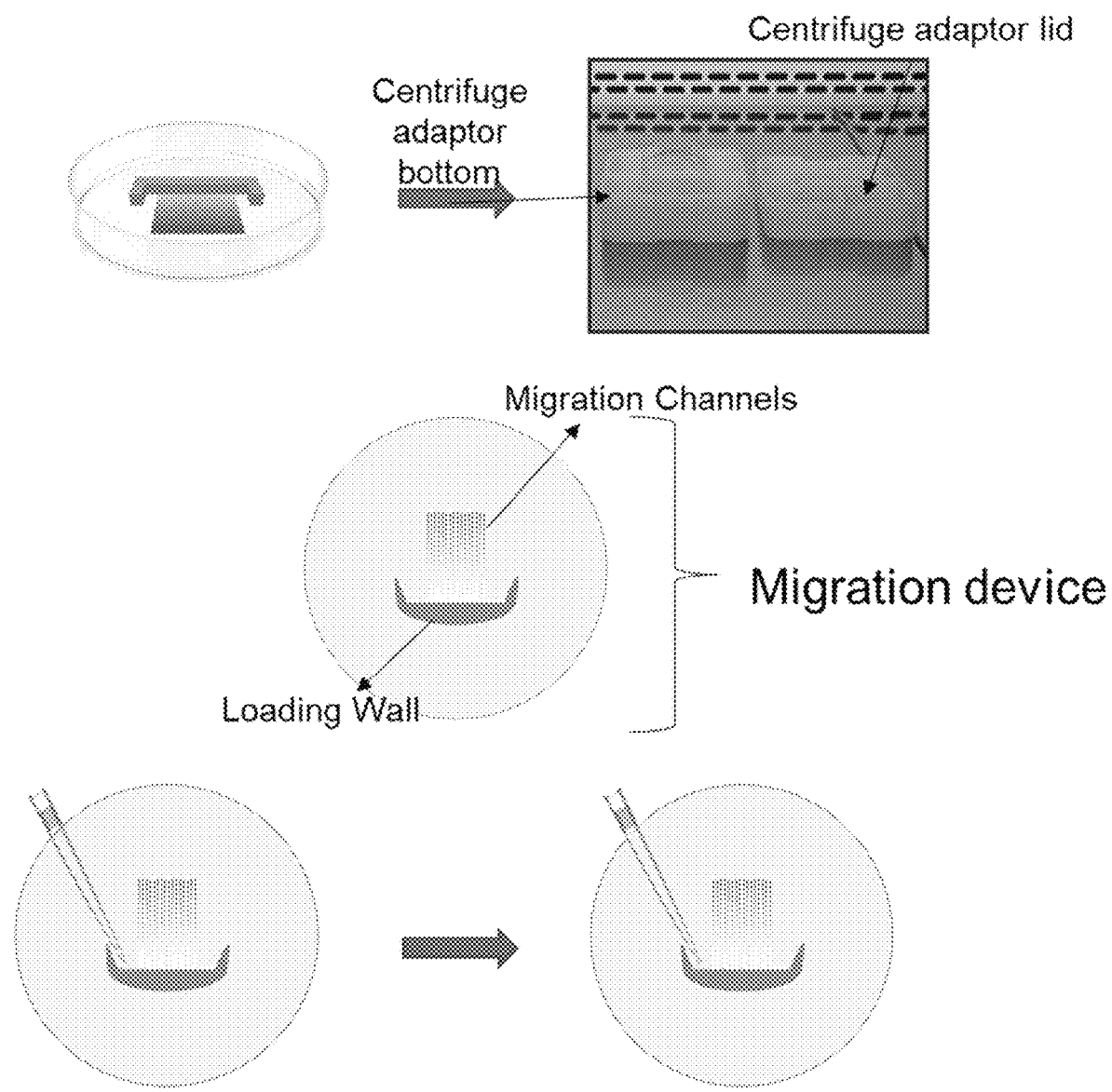
Figure 13:
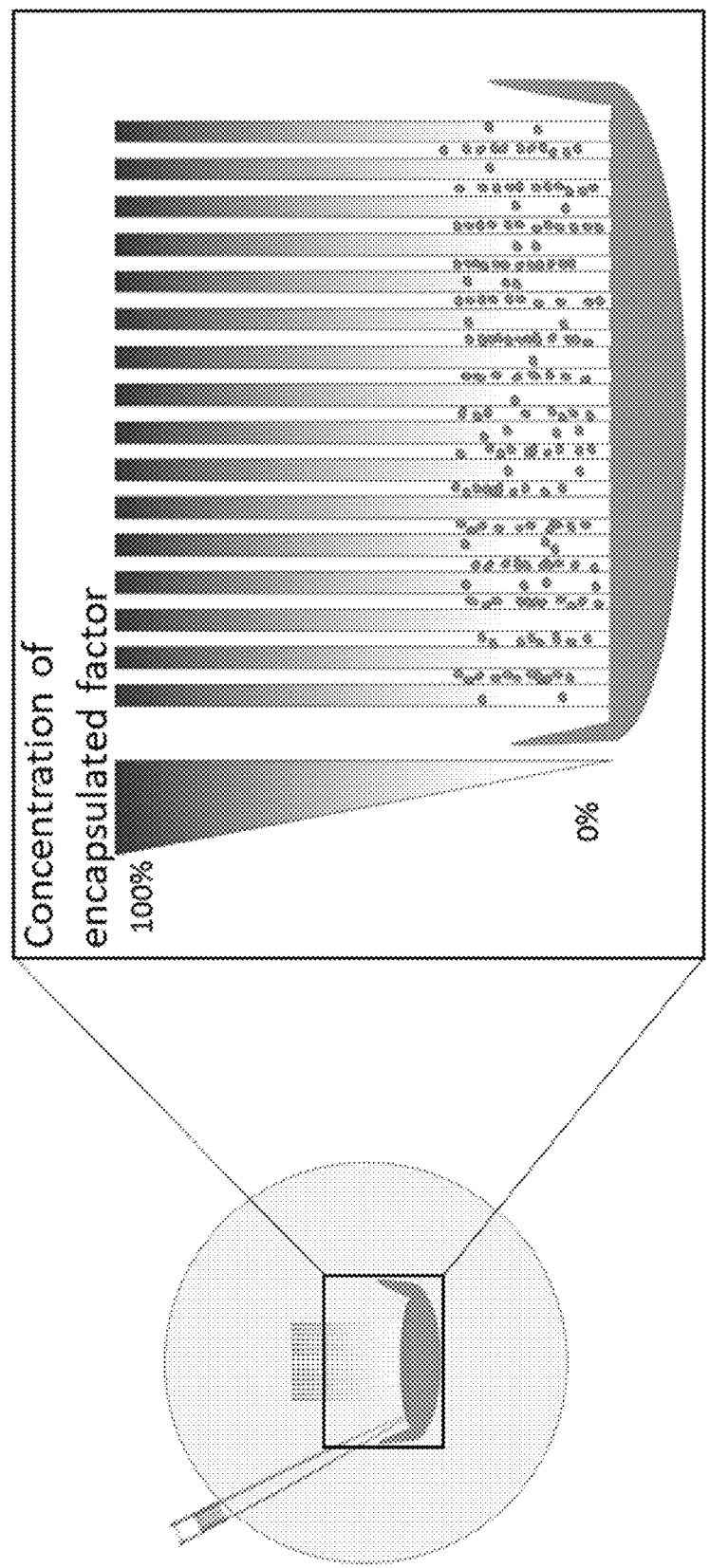
Figure 13:
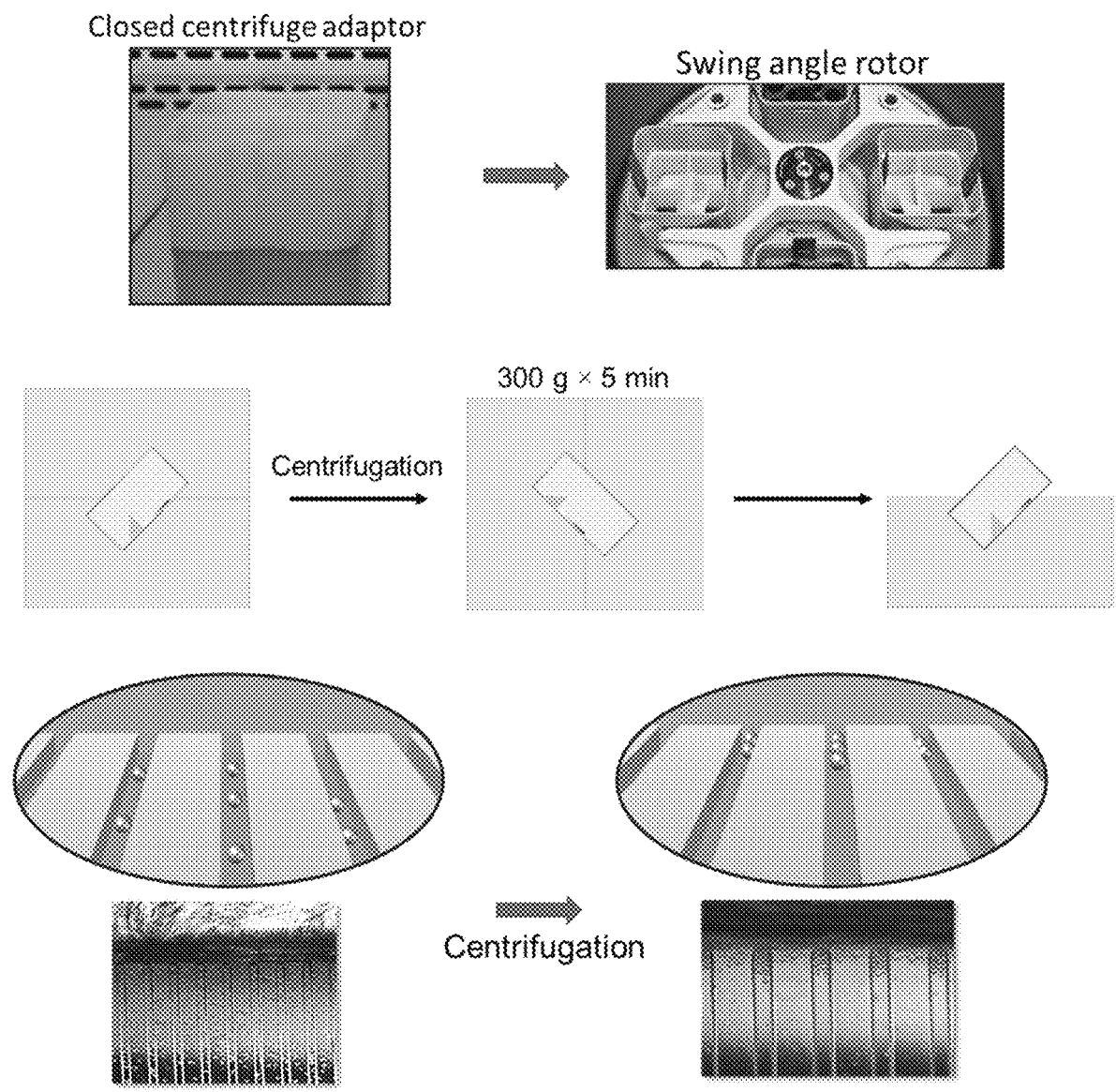
Figure 13:
Figure 13:
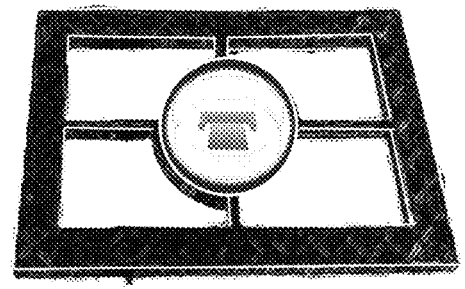
Figure 13:
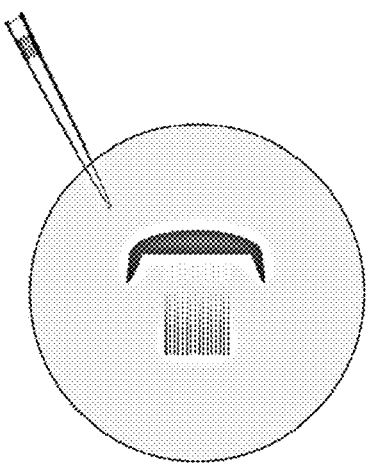
Figure 13:
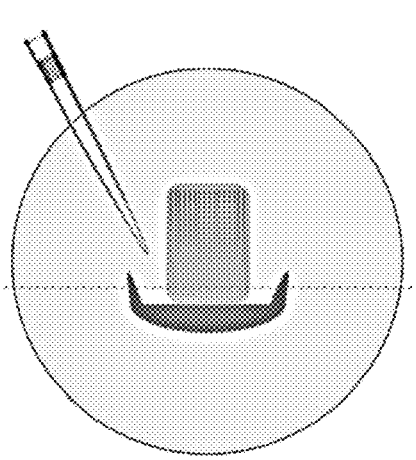
Figure 13:
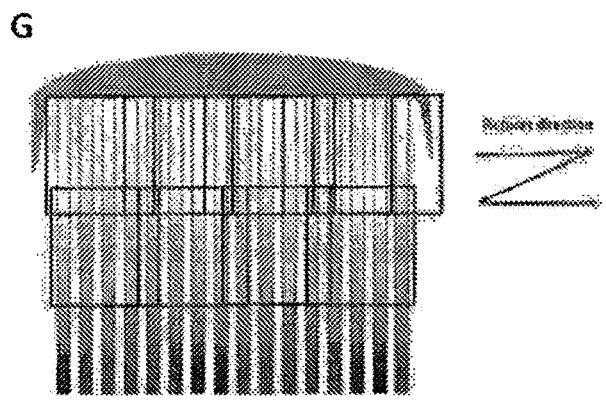

FIG. 13 include seven parts, A, B, C, D, E, F, and G. A illustrates cell loading into the device and the centrifuge adaptor to assist localization of cells at the beginning of the device. B illustrates micropipette loading of cell suspension in device. C illustrates centrifugation component (centrifuge adaptor) of the device as well as illustrates the localization of cells at the beginning of migration lanes after cell loading and centrifugation of the device. D shows the incubator adaptor (top) use to assist the cells attachment in the cell incubator following the centrifugation step. It is shown as well the microscope adaptor for the device used for imaging of migrated cells into the device (bottom). E illustrates washing and incubation after cell attachment in the device, while F shows cell staining process using fluorescent reagent. Finally, G shows imaging the stained cells in the migration device using the microscope adaptor following a series of microscope images with 20% overlapping to help in the digital stitching of successive images of the whole device.

Figure 14:
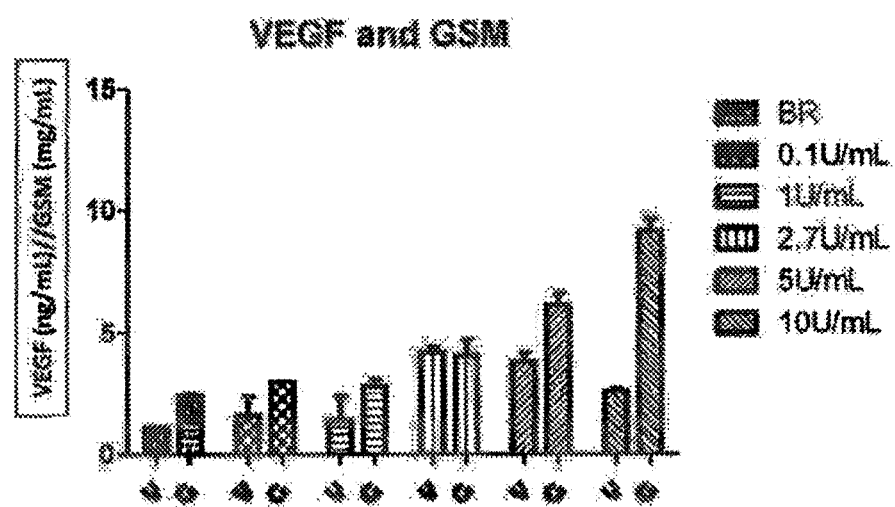

FIG. 14 shows vascular epithelial growth factor (VEGF) and gelatin degradation products (GSM) concentrations released at different concentrations of collagenase (factor release activator).

Figure 15:
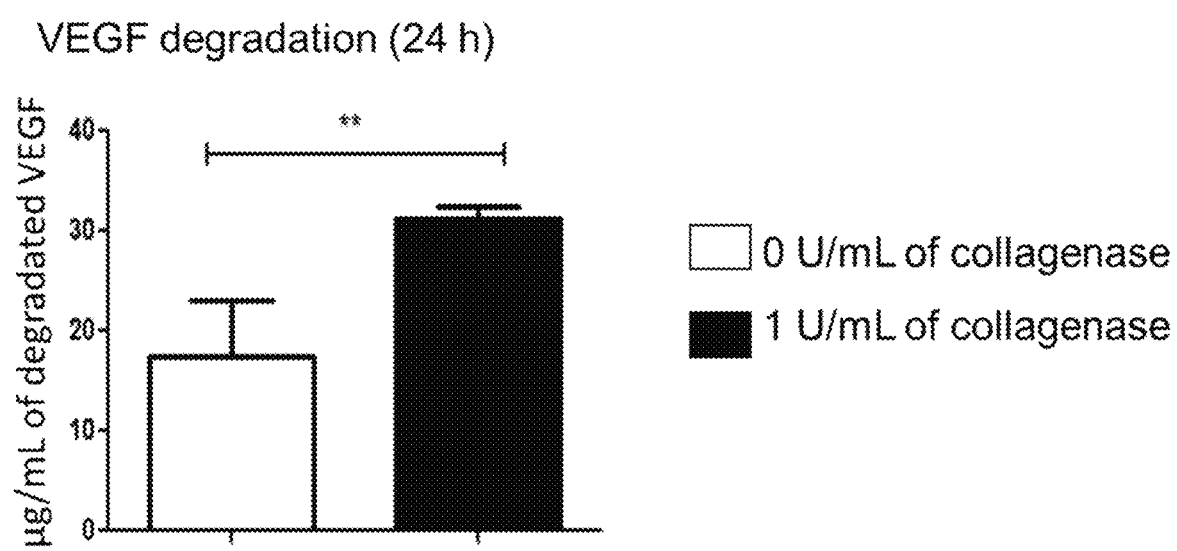

FIG. 15 shows the micro gram per milliliter degradation of VEGF factor with and without collagenase after 24 h incubation at 37° C. in cell culture medium.

Figure 16:
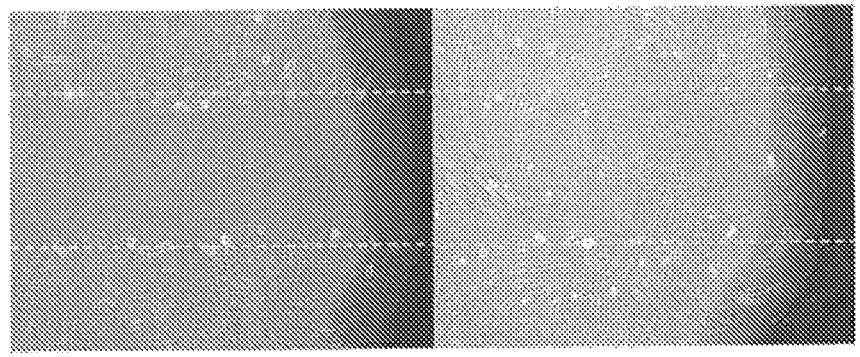
Figure 16:
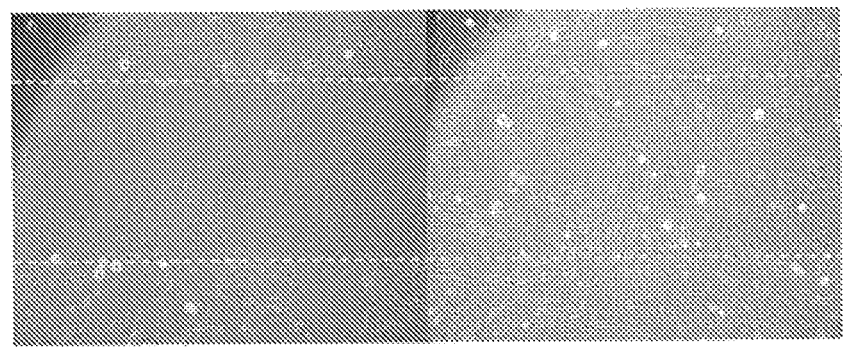

FIG. 16 shows a migration of mesenchymal stem cells from bone marrow (MSCs BM) with and collagenase (release activator) through a scratch assay. Results show no effect on the cell migration performance.

Figure 17:
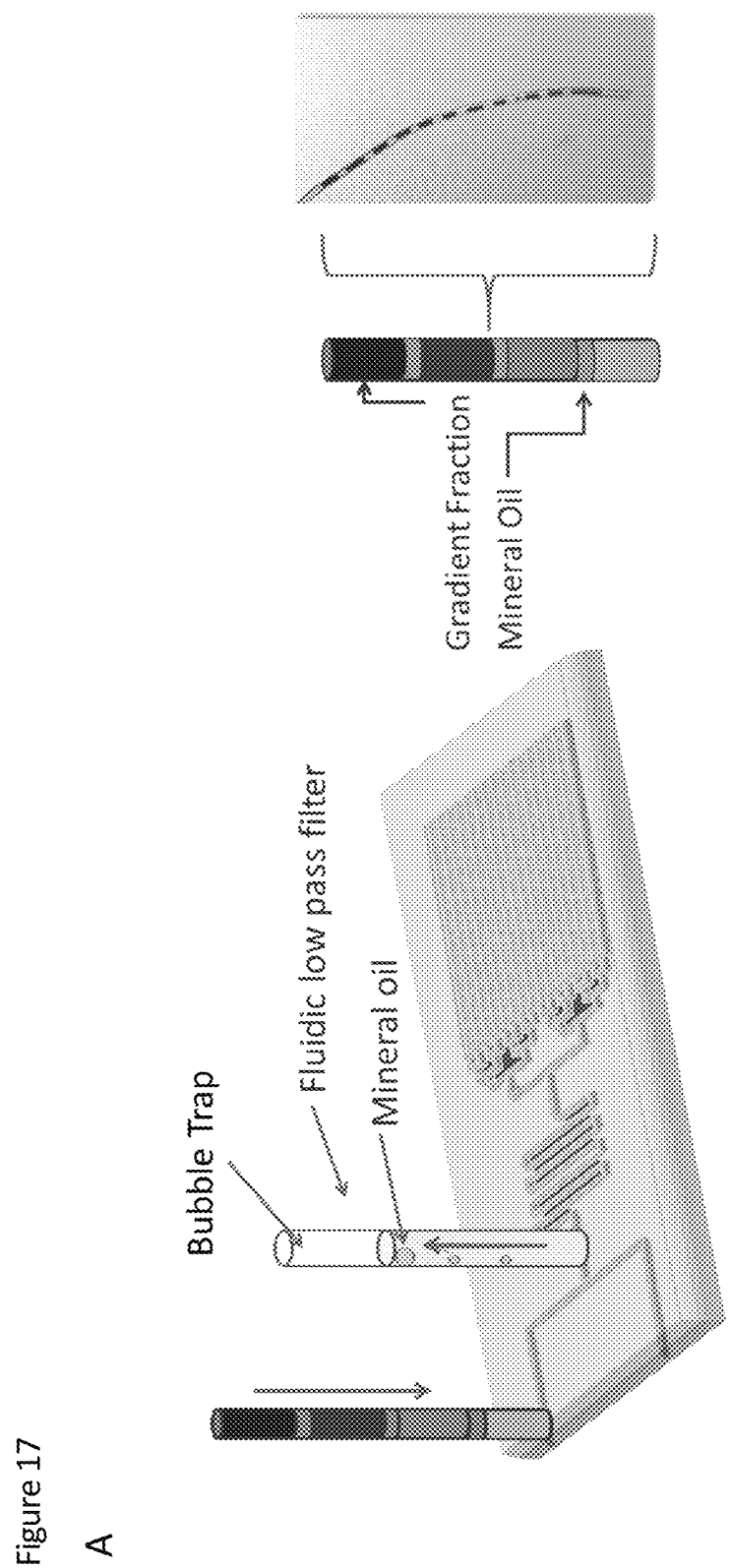
Figure 17:
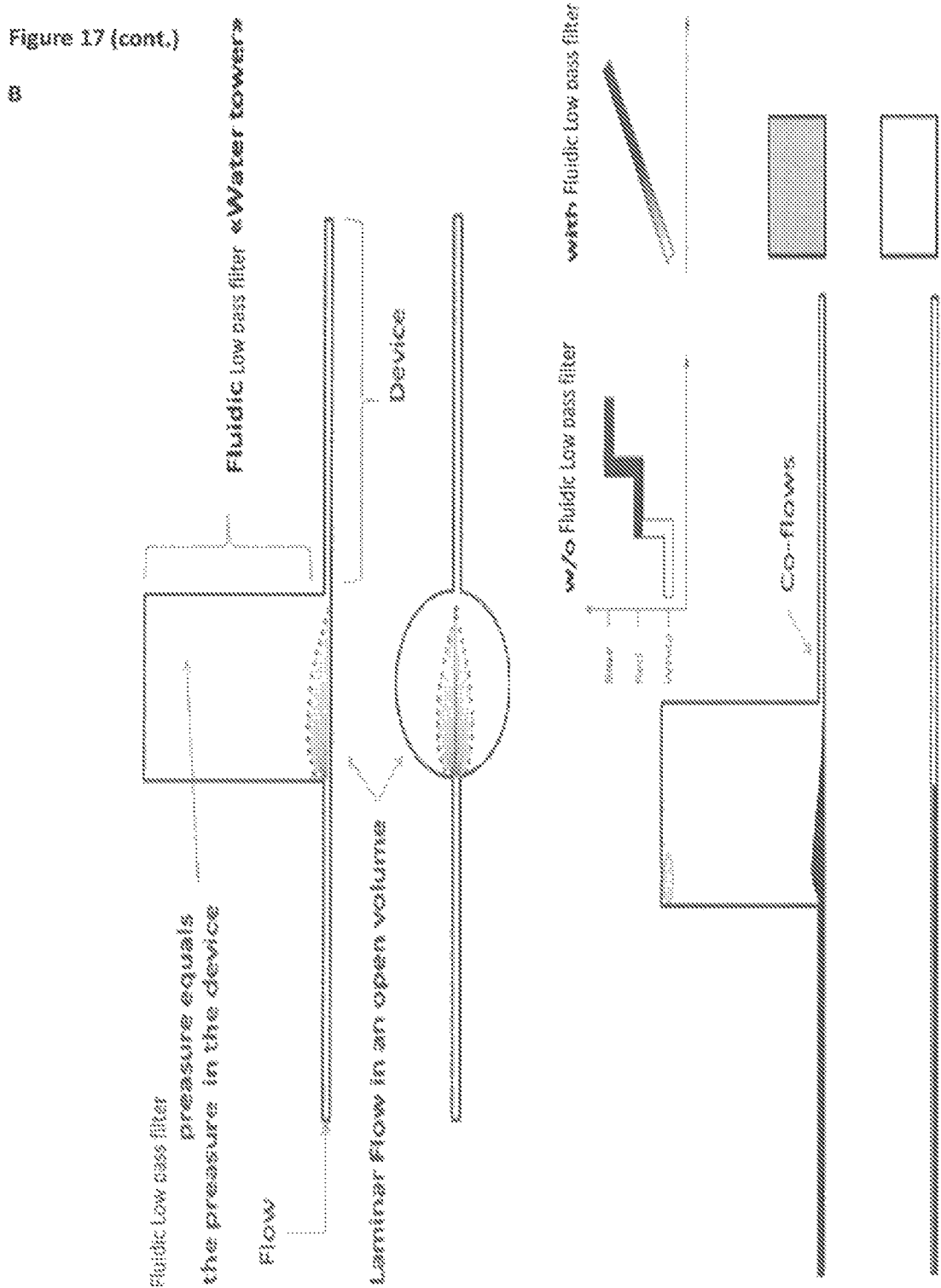
Figure 17:
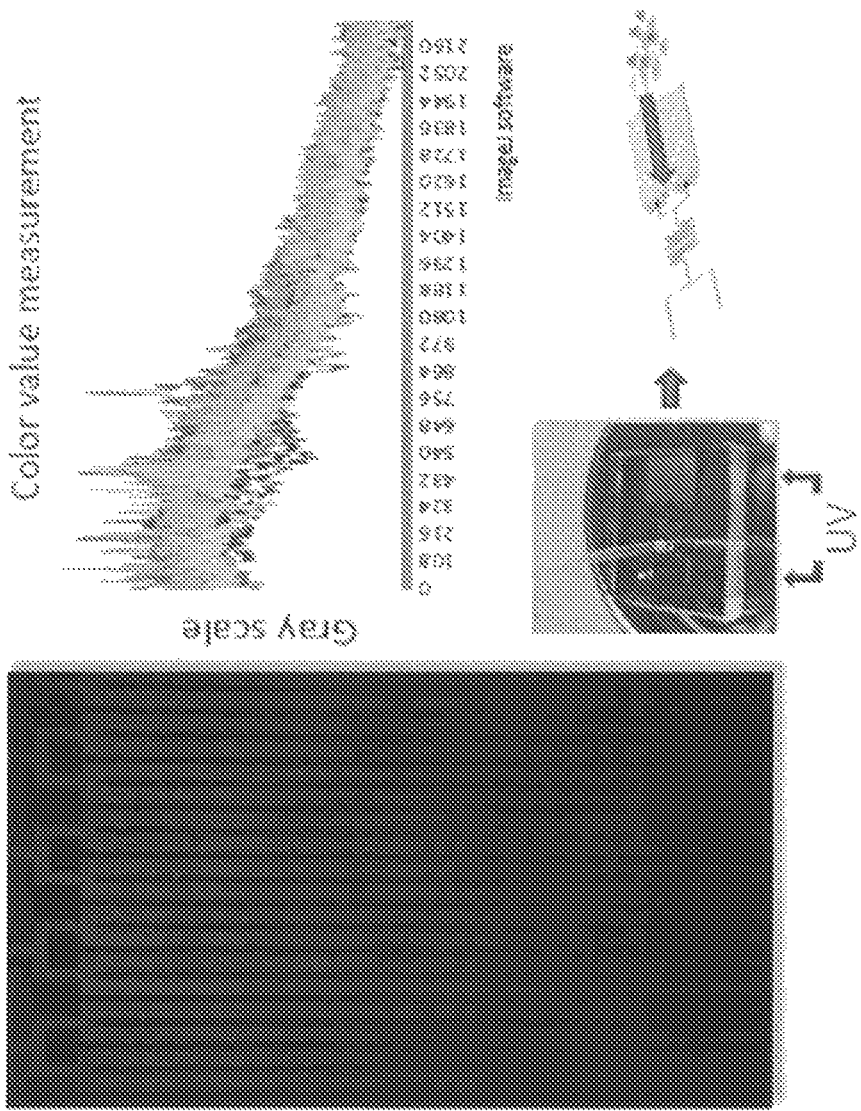

FIG. 17 includes three panels, A, B and C. Panel A shows a schematic of the formation of a stepwise concentration gradient where different concentration fraction is separated by mineral oil. Panel B shows the schematic explanation how the fluidic low pass filter/bubble trap can assist the formation of a continuous linear gradient. Panel C shows the encapsulated linear gradient of a fluorescent protein within the hydrogel walls.

Figure 18:
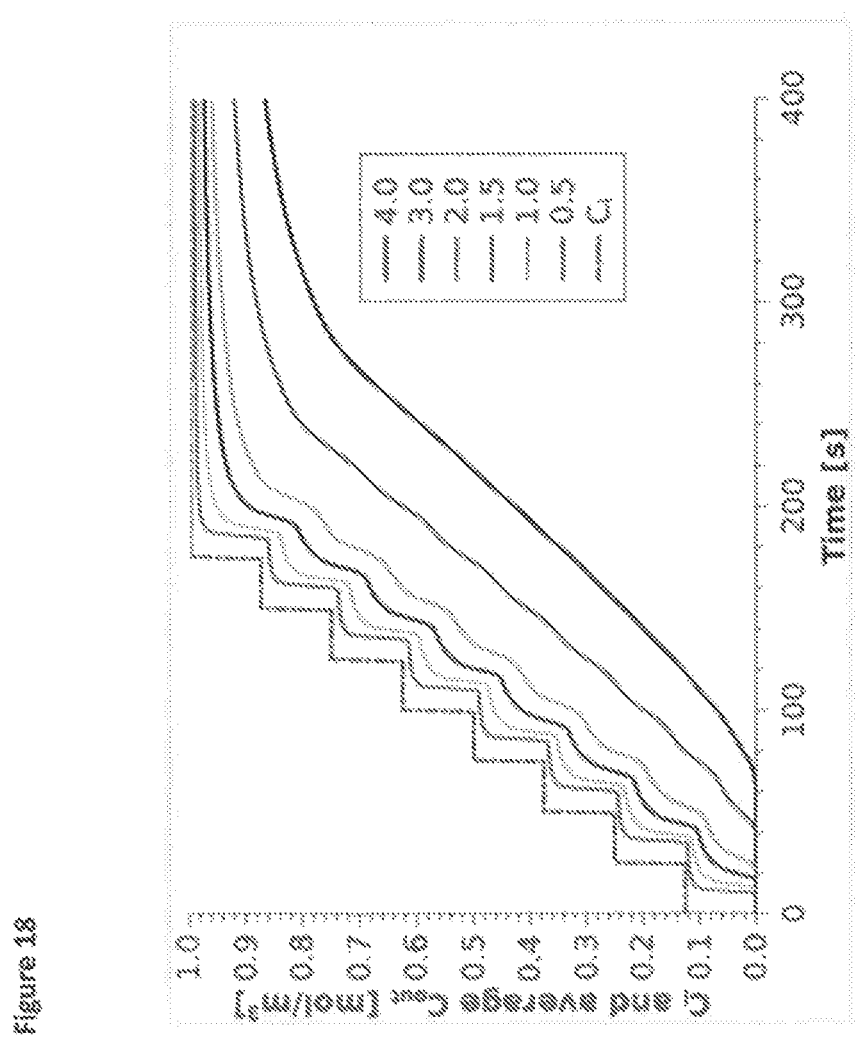

FIG. 18 shows the mathematical simulation of the concentration gradient formation at the parallel channels using fluidic low pass filters fabricated with different diameters.

Figure 19:
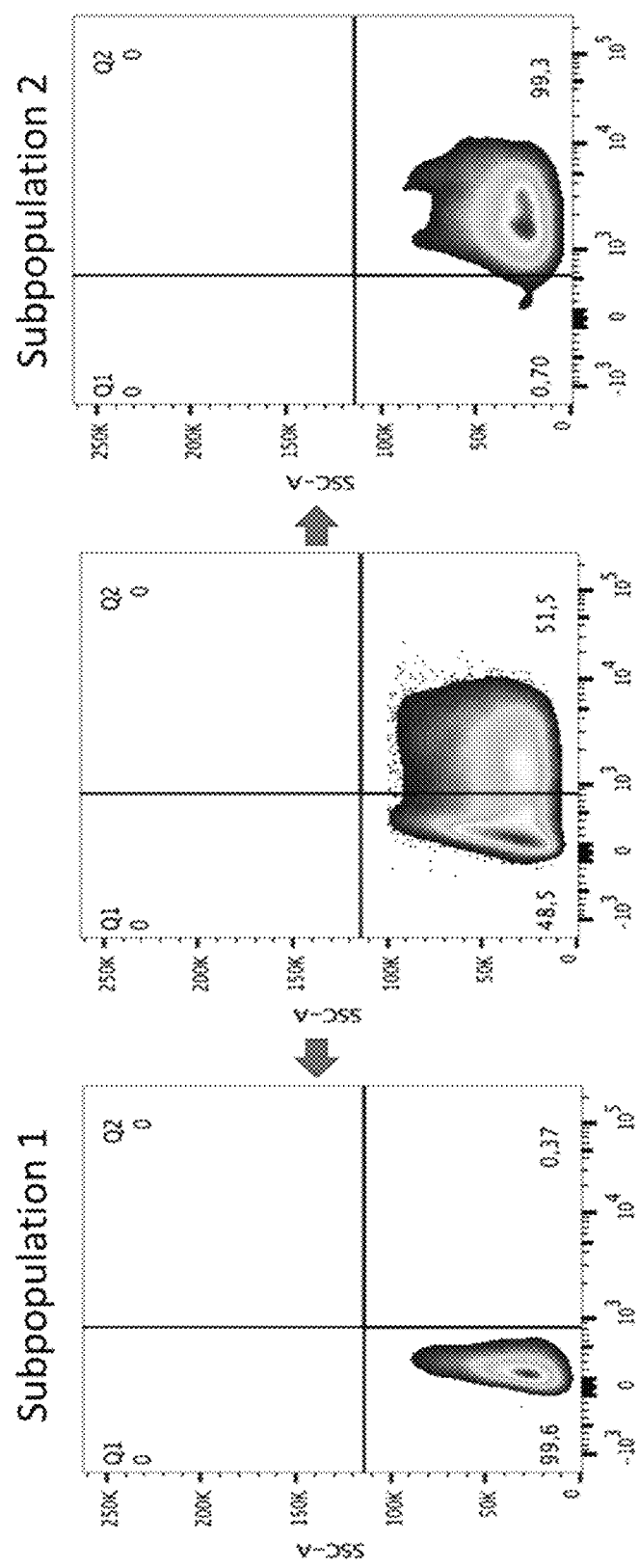

FIG. 19 shows assay results of FACS sorting of two cells subpopulation from a starting mesenchymal stem cells sample. Cell sorting was driven based on the presence or absence of a cell migration related cell surface marker (CD56).

Figure 20:
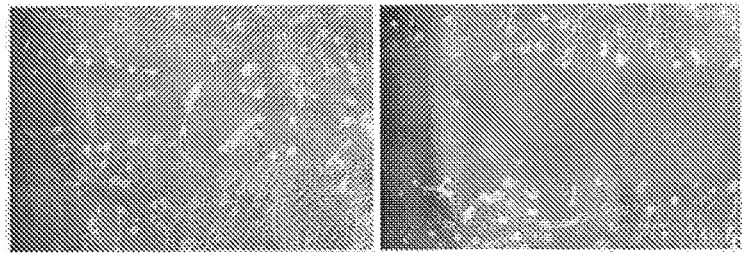
Figure 20:
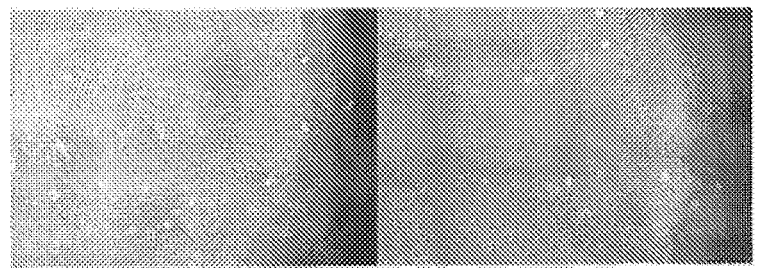
Figure 20:
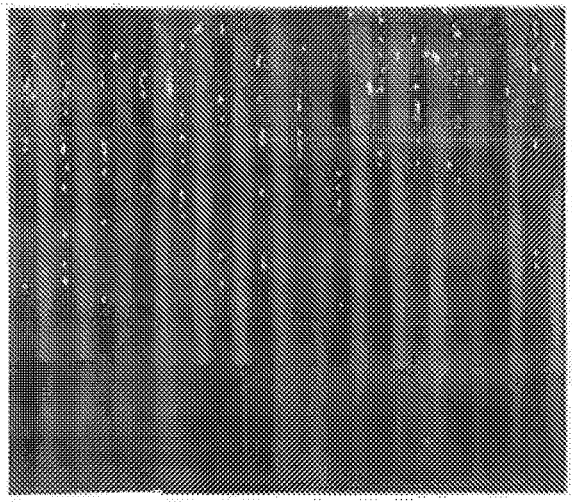
Figure 20:
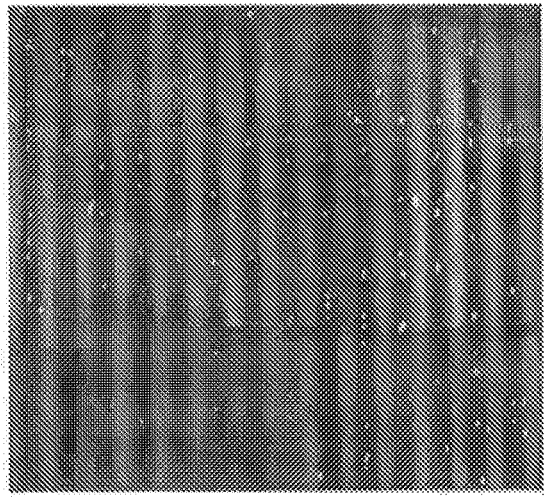

FIG. 20 shows cell migration response of the two sorted cell subpopulations in a scratch assay and using the migration device.

Figure 21:
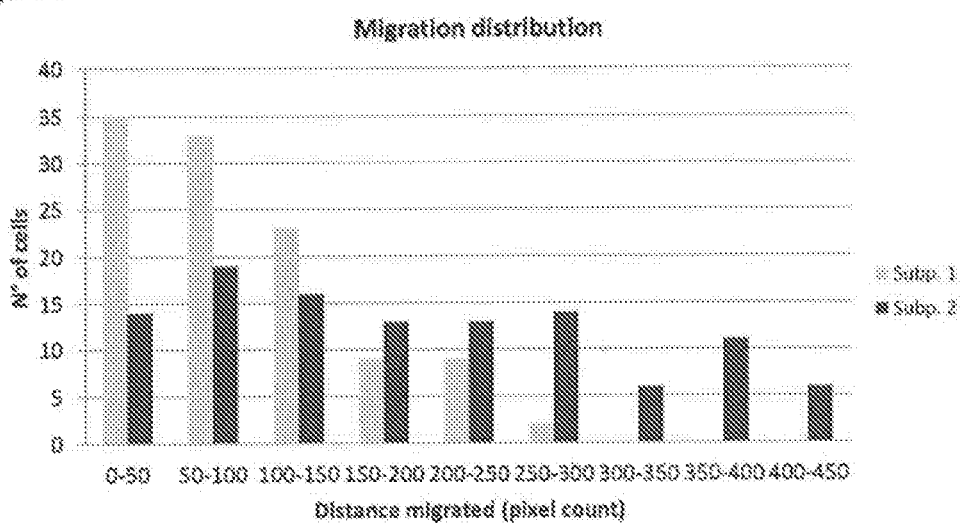

FIG. 21 shows a graphical representation of migration patterns of the two sorted subpopulations.

Figure 22:
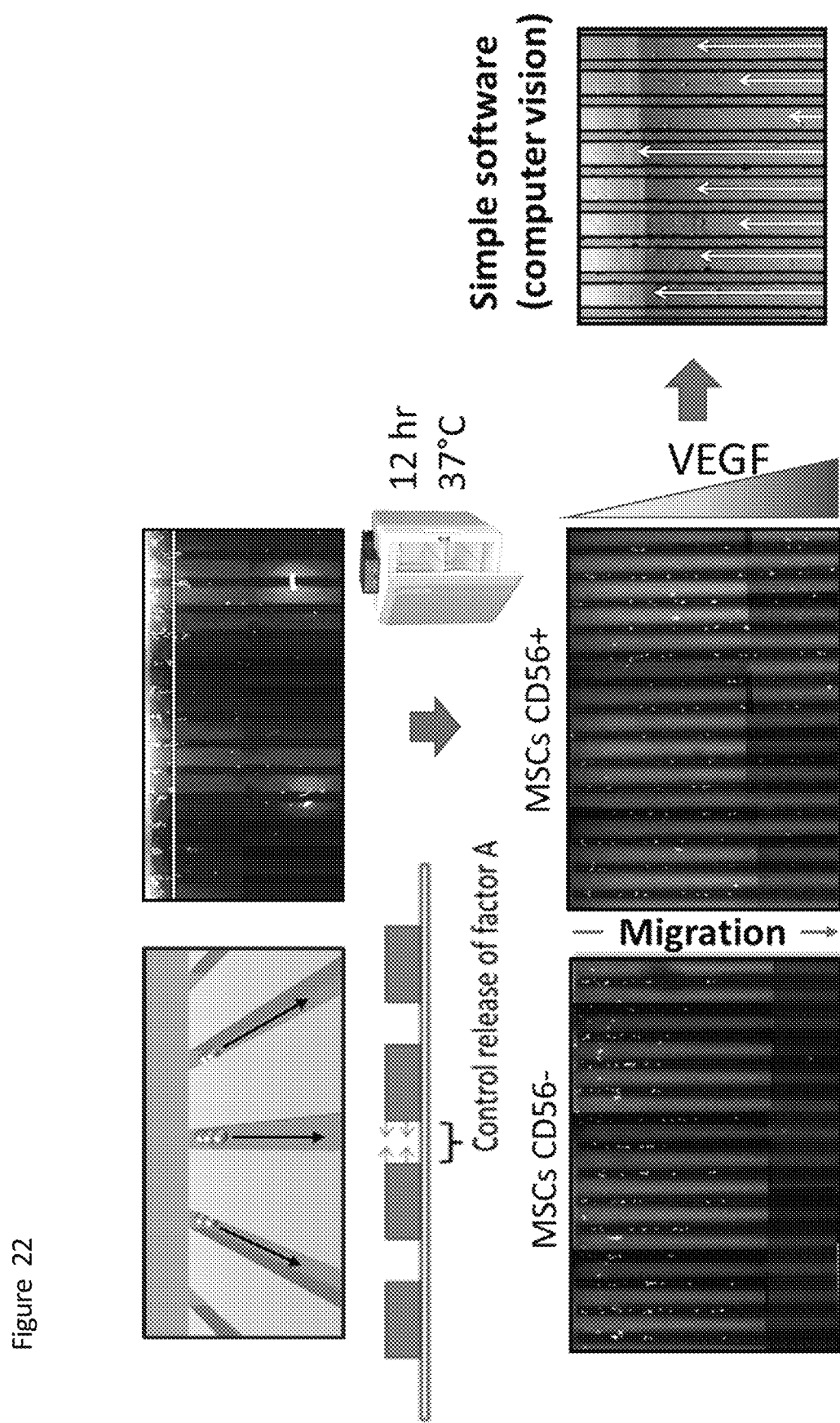

FIG. 22 shows an example of the device functioning using the two stem cell subpopulations. Two stem cell subpopulations distinguished by the presence or absence of a receptor involved in migration response (CD56) were submitted to migration assay directed by VEGF gradient. Clear migration response is observed and analyzed by a simple computer vision software. The algorithm calculated the distance between the pre-established origin of migration (beginning of the migration lanes) and the actual cell position.

Figure 23:
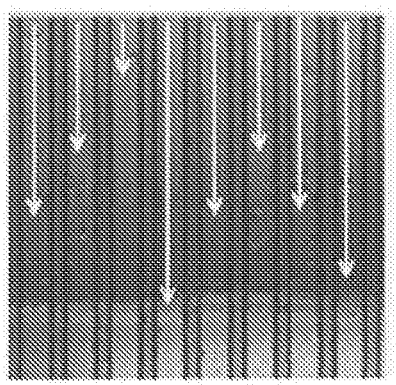
Figure 23:
Figure 23:
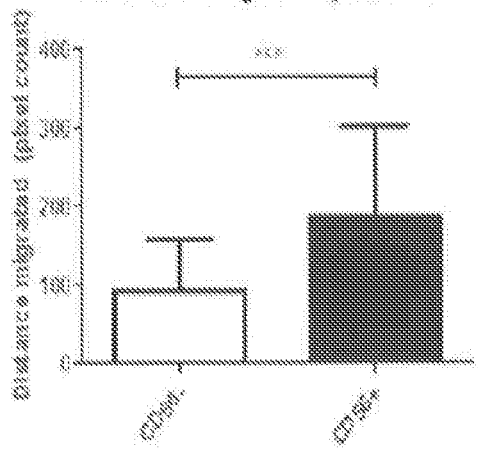
Figure 23:
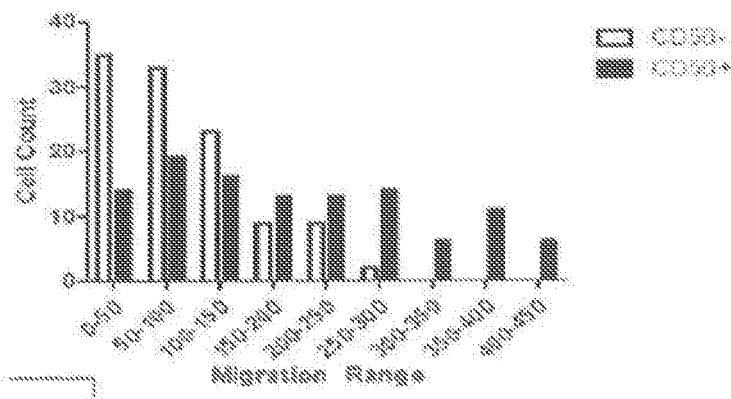
Figure 23:
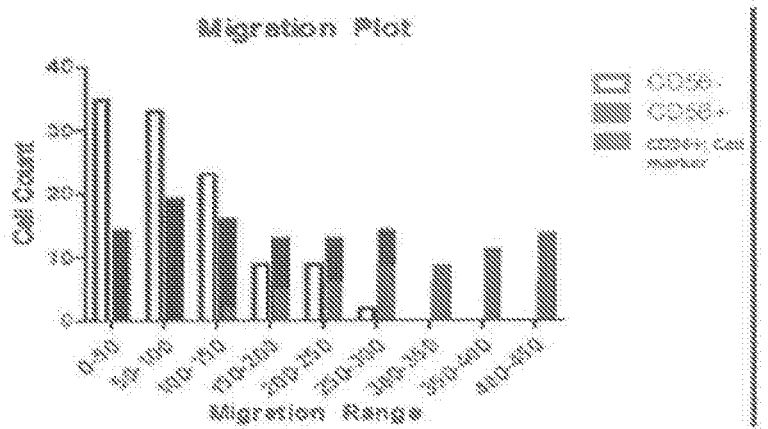

FIG. 23 shows a graphical representation of data acquisition and results to assess distinction of cells with different migration capacity (distribution) in a cell sample. Migration results can be presented as average migration using total data from individual migrated cells, or at a higher level of information showing distribution of migrated distance as shown in the second graft. Interestingly, this evaluate individual cell capacity of migration, reflecting levels of heterogeneity in the cell response. Under continuous device recording, it can give information about the individual cell migration behavior in presence of increasing concentration of the migration-inducing factor. The device is compatible with other cell biology techniques, such fluorescence cell labelling which could report the presence of other biologically active cell elements (receptors, enzymes) or cell activity (cell differentiation, gene transcription).

Figure 24:
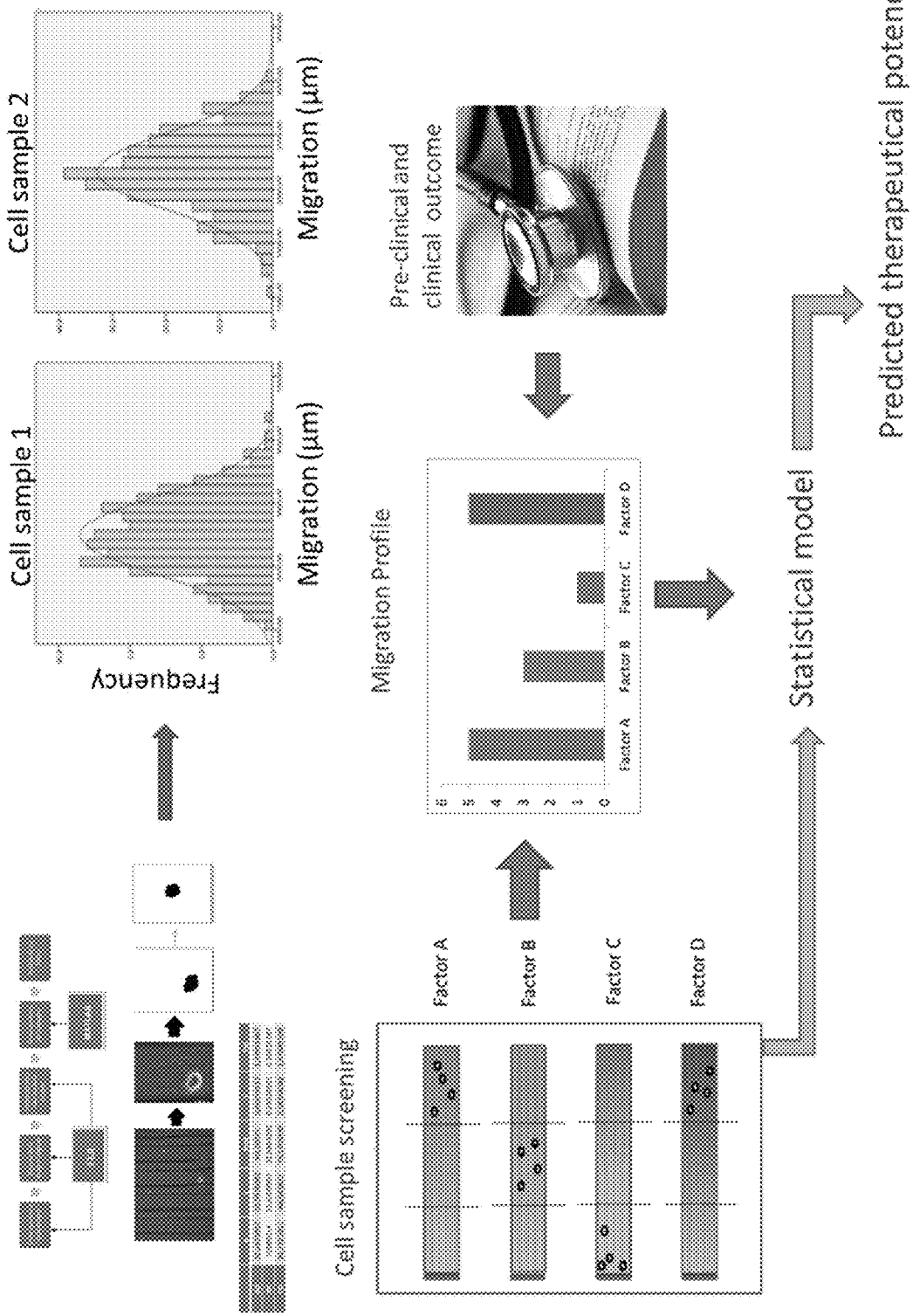

FIG. 24 shows a graphical representation of one embodiment of a potency test for assessing predicted therapeutic potential.

Figure 25:
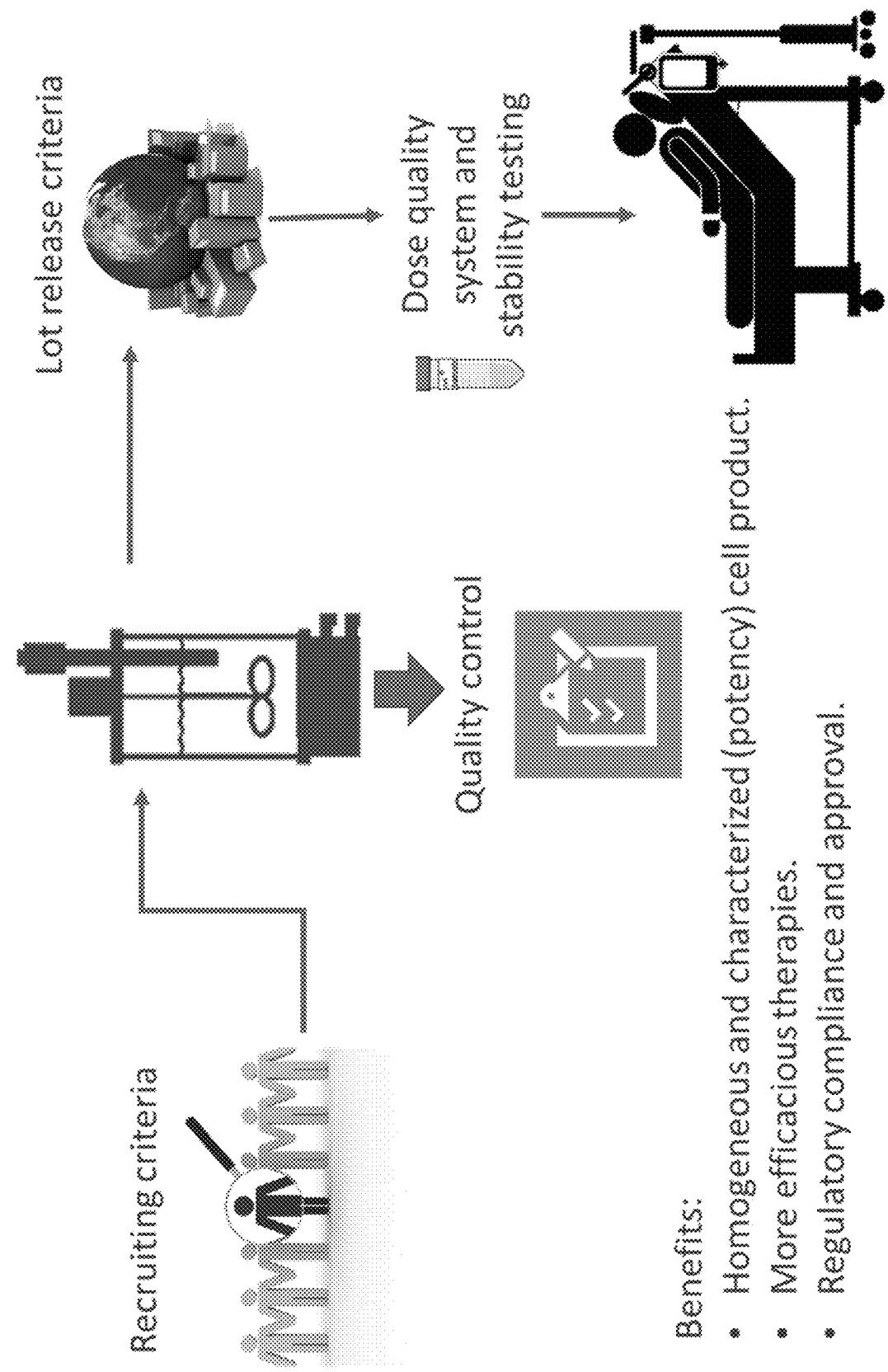

FIG. 25 shows a graphical representation of one embodiment of a potency test for assessing dose quality system and stability testing.

DETAILED DESCRIPTION OF THE INVENTION

I. Cells

As used herein the term "cells" may comprise any variety of cell types including, but not limited to, mesenchymal stem cells, early mesenchymal/stromal precursor cells, adipose tissue-derived stem cells, Muse-AT cells, hematopoietic cells, hematopoietic stem cells, platelets, Kupffer cells, osteoclasts, megakaryocytes, granulocytes, NK cells, endothelial precursor or progenitor cells, pluripotent cells, CD34+ cells, Stro-1+ cells, Stro-3+ cells, CD29+ cells, CD166+ cells, Thy-1+ or CD90+ stem cells, CD44+ cells, immune cells such as monocytes, leukocytes, lymphocytes, B and T cells, NK cells, macrophages, neutrophil leukocytes, neutrophils, neutrophil granulocytes, and the like, adult and embryo stem cells, mesenchymal stem cells (MSCs) corresponding to the three embryo lines (endoderm, mesoderm, and ectoderm). The mesenchymal stem cell may comprise multipotent stromal or mesenchymal cells, early mesenchymal/stromal precursor, or adipose tissue-derived stromal/ stem cells, which can serve as stem cell-like precursors to a variety of different cell types such as, but not limited to, adipocytes, osteocytes, chondrocytes, muscle and neuronal/glial cell lineages. These include osteocytes (bone cells), chondrocytes (cartilage cells), adipocytes (fat cells), myoblasts (muscle cell precursors) cardiomiocytes (heart cells), neurons, and astrocytes (glial cells). The cells may be derived from a cell bank or from the patient in need thereof.

As used herein, the term "differentiated" refers to a cell that has achieved a terminal state of maturation such that the cell has developed fully and demonstrates biological specialization and/or adaptation to a specific environment and/or function. Typically, a differentiated cell is characterized by expression of genes that encode differentiation-associated proteins in that cell. For example expression of GALC in a leukocyte is a typical example of a terminally differentiated leukocyte.

The terms "precursor cell", "progenitor cell" and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, the terms "multipotent", "multipotential" or "multipotentiality" are meant to refer to the capability of a stem cell to differentiate into more than one type of cell.

As used herein, the term "allogeneic" is meant to refer to any material derived from a different mammal of the same species.

As used herein, the term "autologous" is meant to refer to any material derived from an individual or patient in need thereof, and re-introduced to the individual or patient.

Stem Cells:

Adult and embryo stem cells therapeutic potential has been the center of extensive research, although no effective methodologies have been developed for the assessment of their therapeutic quality. The only quick assessment of quality of stem cells to be administered to a patient correspond to cellular stability or feasibility tests (quantification of alive and dead cells), without considering variations in terms of therapeutic capacity between the different cell preparations.

On the other hand, the lack of information on administered stem cell doses is the main cause for variable therapeutic results and failures in clinical tests, which results in the rejection of stem cell use by the regulating entities.

Stem cells actual therapeutic activity depends on multiple biologic activities that include, on the one side, detection and specific response in front of different factors secreted by damaged tissue, migration and implantation capacity in the damaged area and, finally, its regenerative effects that go from differentiation to new functional tissue as the secretion of protecting and regenerating elements for the tissue. Cell homing, which includes the capacity to record damage, migration, and implantation factors, are essential and priority activities to obtain a positive regeneration result. In the event cells are not in a receptive condition with regard to these signals from damaged tissue and are not capable to perform homing, their therapeutic capacity is clearly deficient.

Stromal cells, also called mesenchymal cells, correspond to tissue of mesodermal origin, which supports functional cells forming different organs. This heterogeneous cell population is formed by different cell types, among which we may find fibroblast, different progenitor cells, and mesenchymal stem cells, being fundamental for the good functioning of organs and cells replacement.

Within the adult stem cells, those corresponding to progenitor cells originate different cell types, as in the case of hemopoietic stem cells which, after differentiating, form the different bloodlines.

Among adult stem cells, mesenchymal stem cells (MSCs) especially outstand for being capable of generating different cell types belonging to the three embryo lines (endoderm, mesoderm, and ectoderm). These include osteocytes (bone cells), chondrocytes (cartilage cells), adipocytes (fat cells), myoblasts (muscle cell precursors) cardiomiocytes (heart cells), neurons, and astrocytes (glial cells).

Other MSC characteristics that have made this cell type an interesting candidate for its use in the treatment of different pathologies are: the ability to be recruited to damage tissue through different bio-chemical signals; the capacity to secrete different biologic molecules inducing tissue repair and inhibiting inflammatory reactions in the area, and, finally, their modulating functions on the immune system cells and lacking, at the same time, of immunogenicity (the capacity to generate an immune reaction in response to their own presence). On the other hand, MSCs are of hypo-immunogenic character, which allows its more extensive therapeutic use without causing rejection or incompatibility issues with the host.

In order to better classify the MSCs, the International Society for Cellular Therapy defined that mesenchymal stem cells are only those capable of adhering to plastic under standard cultivation conditions; presenting cellular surface markers such as CD73, CD90, and CD105; lacking CD45, CD34, CD14, CD11 b, CD79α or CD19, and HLA-DR markers, and are also capable of differentiating from osteoblasts, adipocytes, and condroblasts under given in vitro conditions. This definition evidences the high heterogeneity of phenotypic markers and functional capacities of this cellular type.

Scientific evidence seems to indicate that MSCs would be formed by different sub-populations, but would also be marked by the environmental factor present in these cells different sources, which makes them different compared to some of their properties. In the framework of this invention, it is desirable that sub-populations are defined according to their therapeutic role or capacity and migration profiles in front of given factors.

MSCs heterogeneity and not having the necessary information to standardize cellular therapies based on adult stem cells, evidences the convenience of developing a quick in vitro test that allows forecasting the therapeutic power or function. This becomes even more notorious if we consider that the only efficient system for the classification and isolation of sub-populations occurs through differentiating transcriptomic or proteomic classification using expended colonies resulting from individual cells. This strategy is not clinically practicable due to its long process, cost of the study, and modifications suffered by these cells' functions after an extensive proliferation.

Due to the fact that MSC samples isolated from different sources are apparently formed by an indeterminate number of sub-populations, researchers in the stem cells area frequently submit their samples to classification of colonies coming from individual cells, in order to individually classify them as different sub-populations. In order to identify these colonies as different cell types, a variety of strategies or criteria have been implemented, such as grouping based in new markers for cytometry, transcriptomic and proteomic profiles, morphology parameters, cell size, and proliferation speed. However, this criteria are still little efficient to isolate and classify sub-populations, and they do not allow associating individual sub-groups to a given functional role or therapeutic potential.

Another criterion to characterize colonies coming from individual cells is differentiation capacity. Colonies showing good therapeutic activity for certain pathology or damaged organ frequently show differentiation capacity regarding the cell types forming the said organ. There are several examples in literature that rank from osteocyte and chondrocyte differentiation to differentiation of cardiomiocytes, neurons, skeletal muscle, insulin producing cells, and epithelial cells from renal tubules. It is interesting to note that these works show the existence of certain sub-populations that are better adjusted to repair specific tissues; however, no rigorous test has been performed where the multiple differentiation capacity is tested using the same colony. More than an attempt to calculate specific sub-populations, these works identify particular and unique cell groups with a specific potential, without being capable of defining whether they are part of a unique sub-population or a sub-population group sharing the same tested potential.

II. Methods of Assessing Cells

Migration

Cell migration is considered a cell response derived from multiple biological activities and cell signaling. It has a key role in the efficient delivery of stem cells or progenitor cells to injury sites in regenerative processes, cancer metastasis and immune response among others. The process begins with a cell attractant stimulus being tested by the cell receptors. This is translated into migration activation comprising polarized cytoskeleton modification, extension or retraction of cellular protrusions, cell-extracellular matrix (ECM) interaction through adhesion points formation in one side and simultaneous cell detachment on other cell sections. This polarity and movements are spatially restricted by the ECM arrangement, which at the same time provides the cells with a path for the directed cell movement.

One embodiment of the migration device may have a migration path or classic channel via (FIG. 1) or a route system (FIG. 5) with an encapsulated stable gradient in a hydro-gel or other material; this gradient also allows metering encapsulated compounds to the cell migration area (drug delivery).

In the event the factor would induce a repelling response, the gradient would have an opposite direction, presenting lower and lower concentration as the cell advances inside the device.

In some embodiments, the device has a cell sample load system, which facilitates the cells lineal ordering, perpendicular to migration channels (FIGS. 1, 6, 7, and 8). This allows starting, after removing any barrier that keeps the cells orderly in line, the migration stage ensuring that all cells are at the same point regarding the migration axis. The load chamber may be developed through different strategies aligning cells and preventing their free distribution before the test start. These load chambers may or may not require to be removed before the migration start (FIGS. 1 and 7) and (FIGS. 6 and 8), respectively.

After migration, the sample cells migration distance is calculated (score), and then values are included in a statistics mathematical model specific to the cell type and pathology.

This includes the attributes or factors that explain the cells therapeutic response in front of a given pathology, and previously researched, identified, and forming part of the assessment platform.

Cell Adherence

Figure 2:
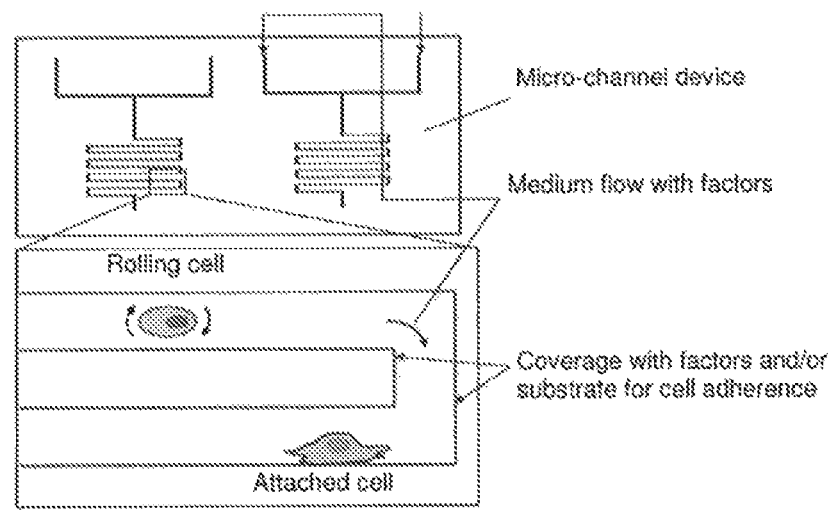
FIG. 2 shows elements forming an assessing device for the cell response adherence include a micro-channel circuit for the perfusion of a liquid medium containing certain adherence inducing factors; an internal substrate that limits the channels edges, which may contain coverage to facilitate cell adherence and/or present or release adherence inducing factors; and the entry for a liquid medium injection containing or not the cells from a sample.

The second cell adherence assessment device (FIG. 2) is formed by a micro-channel circuit that allows a particular sample cells flow, and may be performed in the presence of different factors capable of inducing cell adherence on these micro-channels' walls. The device includes two entries, one for the intake of a cell flow re-suspended in a medium that preferably and slightly inhibits cell adherence, and a second entry where a flow is injected from a medium with adherence inducing factors. The adherence inducing medium flow is combined with the cell flow in a back area in the channel circuit (see example in FIG. 2), this way promoting adherence of cells contained in the sample.

Micro-channels' walls may be covered or not with a substrate that facilitates cell adherence, such as hydro-gel or other material with the capacity to host cell adherence and/or release adherence inducing factors, or substrates absorbed on the channels surface allowing general or specific cell adherence of certain cell types, or with the adsorption of cell adherence inducing elements.

Once the cell sample total flow has been completed, which may take from 15 to 45 minutes, a group of cells would have responded by adhering and staying inside the device. Quantification of a cell sample adherence capacity in front of certain inducing factors is related to the number of cells withheld within the channel circuit. Later, these values are included into the analysis platform in a statistics mathematical model specific to the cell type and pathology, in a similar way to that expressed above regarding the first device.

As shown in FIG. 4, inside the device, gradient elements and physical restriction of migration lines or lanes may be defined by exclusive cell adherence areas, with no need to include hydro-gels or other materials limiting the cells lateral mobility. This may be realized through the creation of patters defined by adsorption, covalent binding, or other methodology to present a cell adherence substrate. Besides, and through similar methodologies, it is possible to include migration inducing factors growing gradients in these adherence patterns.

III. Methods of Assessing Therapeutic Potential

For the assessment of therapeutic potential regarding each pathology, there is a set of factors that may be included into the hydro-gel or material contained in the migration device, or perfused, or included in the channels in the case of the cell adherence device. Kits for the assessment of a specific sample also include an incubator, stain and fixation solutions, a microscope adjustable to a telephone camera (for instance, iPhone), as economic option. The analysis platform receives the information through a photograph of the image shown by the microscope, which is analyzed using a program or algorithm that includes computer display elements that allow obtaining the migration score or quantification of adhered cells. Later, data quantified from the images and coming from assays in the presence of different previously defined factors are included in a statistics model that provides the user a predictive value of a cell sample therapeutic potential for the treatment of a specific pathology. Based on this data, a predictive value of the possible functional recovery of tissues or organs affected by the pathology is obtained.

According to this invention, a device and/or kit are applicable in the following areas:

A. Applications

Cell Banks:

Currently, cell banks provide storage service for stem cell whose properties and therapeutic power are unknown. Before storing the sample, the device could be used as recruiting criterion and for the assessment of the collected sample therapeutic characteristics. Therefore, the correct methodology or device allows gathering information on cell potential, in addition to obtaining a detailed list of cell responses (migration/adherence) in front of different factors, a response that could be correlated to potential therapeutic uses in a variety of pathologies. Information on the collected cells quality would allow clients to make informed decisions, as repeating cell collection or seeking better cell sources for collection and storage. This would give an added value to the service currently offered by cell banks.

Cell Therapy Equipment in Clinics and Hospitals:

The use of the device in these institutions should be useful as therapeutic quality control before therapy and after thawing the sample. In institutions authorized to isolate and/or expand patient cells for their later injection to the same patient (autologous therapy) these devices could control the cells good conditions in different stages of the process, optimizing protocols and ensuring better therapeutic results for patients. Besides, the device will be used to study cell potential of patients who need treatment in order to radically shorten the mesenchymal cells study for cell therapy, which in a normal laboratory could take one year compared to the two days it takes using the devices or kits.

Research:

Research centers could use the device for the testing of different cell types, isolation and expansion protocols, effects on therapeutic quality in the presence of different treatments, etc., in order to continue advancing in cell therapy. This tool could be used to standardize experimental conditions with stem cells; for instance, to quantify cell effects in the presence of different treatments or conditions, etc. This device could be simply used for efficient and robust migration assessment in any research filed that involves cell migration or cell adhesion.

Cell Therapy Companies and/or Cell Products:

These devices could have a series of great value uses in these companies' production processes and businesses. A device validated for a given pathology or therapy may be used as a quick recruiting criterion for donated cells that would be the raw material for the production of many therapeutic doses after their expansion. This could ensure that donated cells will always have a given quality, as well as their homogeneity and the therapeutic effect of different production batches. During the expansion process, these devices could be used to ensure a uniform therapeutic potential for each one of the cell doses as they expand to generate a large number of doses. Also, their use could serve as criterion to optimize production processes for a given cell product. Once the cells have expanded and generated the production batch, these devices are capable of assessing whether the cell product meets the therapeutic quality criteria established, and decide whether the production can be released to the market. Generally, therapeutic doses are transported to the application points in different ways; one of them is through frozen flasks. Companies establish thawing and preparation protocols for the doses, which are carried out before administration to patients at the therapy location. These devices are capable of controlling cell quality before their use in patients in order to ensure that the transportation, thawing, and preparation process was correctly carried out, without affecting their therapeutic effectiveness on patients. The importance of this type of devices in this type of companies is very important and has become a requirement imposed by regulatory agencies for this type of therapeutic products.

IV. Advantages

The migration device is easy to use and capable of predicting adult stem cells therapeutic potential in 8-12 hours to 2 days, or lower time periods, (depending on channel geometry or distribution in the device) with 90% accuracy rate. The device also uses a very low cell number (less than 500 cells) compared to other classic techniques such as flow cytometry and ELISA tests.

In the case of the adherence assessment device, the therapeutic potency assessment may be carried out in 15 minutes to 2 hours, and it also requires a minimum number of cell samples (less than 500 cells).

According to the present invention, devices assess cell migration or adherence in the presence of factors that can be correlated to the success rate in different treatments, such as recovery from acute kidney damage or other pathologies. They also allow calculating a cell sample or product therapeutic variability according to the activity presented by cells in the devices and estimating the cell dose to be administered to a patient when treating a given pathology, among other high value applications.

Reading results is a simple counting process of the number of cells that migrated to each factor or that adhered in the presence of each factor (as may be noted in FIG. 9). This value may be used by cell therapy product companies, blood banks, cell therapy centers, or specialized medical groups.

As a support for result analysis, a platform is used with a mathematical model to weight the number of cells that migrated to each factor or that adhered, with a rate that represents the factor correlation with damage recovery or therapeutic effectiveness. With this, it is expected to calculate whether a cell sample will be useful or not for the pathology treatment. This radically changes a given pathology treatment scenario, considering that use of these devices will guarantee the success of the patient cell therapy, preventing acute pathologies passing to chronic or more advanced stages and increasing regenerative therapy success.

Other advantages solved the following unmet needs: 1) linear, well-established and controlled gradient of migration-inducing factors; 2) easy and robust quantification of cell migration; 3) real-time imaging of the cells while they are migrating; 4) easy measurement of cell velocity, directionality and migration index; 5) capability to distinguishes between chemotaxis and random movement; 6) requirement of simple one (or few) step protocol; 7) 3D cell culture environments; 8) capability of co-culturing of multiple cell types in motility assays; 9) removal of the variability; and 10) flexibility to address different cell types and applications.

V. Device and Platform

Figure 1:
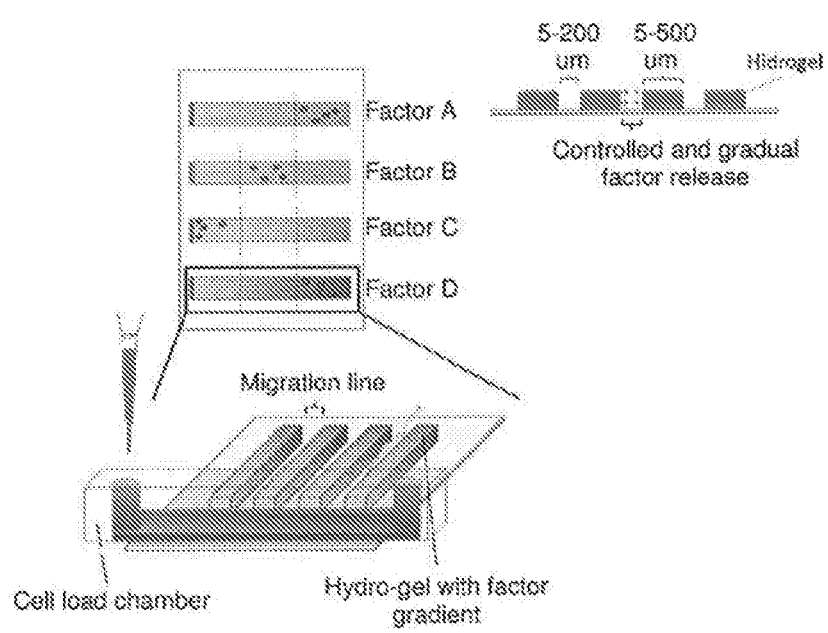
FIG. 1 shows elements forming an assessing device for the migratory response include a cell charge camera that allows adherence of a cell strip perpendicular to the migration lanes; migration lanes or lines that correspond to cell mobilization space left between two hydro-gels running along the device; hydro-gels with an encapsulated factor gradient, which releases, in a controlled way, the factor to the migration space. This way, migrating cells appear with higher concentrations of a given factor as they advance inside the device.

Migration Device:

As described above, the device has a series of parallel assay lanes or lines formed by parallel hydro-gel or other material bands delimiting the cell migration area (FIG. 1). As used herein, the assay lanes or lines may be referred to migration lanes or lines. Likewise, the assay channels may be referred to as migration channels.

In some embodiments, the migration lanes or lines comprise a width of about 1 µm, 2 µm, 3 µm, 4 µm, 5 µm, 6 µm, 7 µm, 8 µm, 9 µm, 10 µm, 12 µm, 14 µm, 16 µm, 18 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 1050 µm, 1100 µm, 115 µm, 120 µm, 125 µm, 130 µm, 1350 µm, 140 µm, 145 µm, 150 µm, 155 µm, 160 µm, 165 µm, 170 µm, 175 µm, 180 µm, 185 µm, 190 µm, 195 µm, or 120 µm. In some embodiments, the migration lines or lanes is 150 µm. The cell migration lines or lanes are each spaced at an equal distance to form at least one migration channel. Such migration channels may comprise 5, 10, 15, 20, 25, 30, 35, or more migration channels. In some embodiments, the number of migration channels is 15. In some embodiments, the migration channel width may be about 1 µm, 2 µm, 3 µm, 4 µm, 5 µm, 6 µm, 7 µm, 8 µm, 9 µm, 10 µm, 12 µm, 14 µm, 16 µm, 18 µm, 20 µm, 22 µm, 24 µm, 26 µm, 28 µm, 30 µm, 32 µm, 34 µm, 36 µm, 38 µm, 40 µm, 42 µm, 44 µm, 46 µm, 48 µm, 50 µm, 55 µm, 60 µm, 65 µm, 70 µm, 75 µm, 80 µm, 85 µm, 90 µm, 95 µm, or 100 µm. In some embodiments, the channel width is about 50 µm. In some embodiments, the channel height may be about 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, or 100 µm. In some embodiments, the channel height is about 50 µm. In some embodiments, the channel length is about 1 mm, 2 mm, 3 mm, 4 mm, 5 mm, 6 mm, 7 mm, 8 mm, 9 mm, 10 mm, 12 mm, 14 mm, 16 mm, 18 mm, 20 mm, 22 mm, 24 mm, 26 mm, 28 mm, 30 mm, 32 mm, 34 mm, 36 mm, 38 mm, 40 mm, 42 mm, 44 mm, 46 mm, 48 mm, or 50 mm. In some embodiments, the channel length is 10 mm.

Forming of lanes is a system open in the upper part, while migration delimitation is in the lower part and previously mentioned side structures. The lower part could be made of glass, polystyrene, or other material capable of structurally supporting the side bands and allowing cell adherence and migration. With regard to side bands, if their function is purely structural limiting structural migration, their composition could be a natural or synthetic hydro-gel of a variety of formulas or a polymer material capable of defining these side bands.

Some natural hydro-gel examples could be based on gelatin, hyaluronic acid, alginate, agarose, chitose, gellan gum, and/or collagen. Some synthetic hydro-gel examples could be based on polyethylene glycol, polyethylene acid, polyvynylpirrolidone, polyacrylamide, and polymetyl methacrylate, among other. In some embodiments of the device, hydro-gel includes a polyethylene glycol dyacrilate based formula (PEGDA), supplemented with pentaerythritol triacrylate (PETA), acrylic acid, and/or acrylamide. In some embodiments, the hydro-gel comprises at least one migration inducing factors (set forth below) or combination thereof. In some embodiments, the hydro-gel comprises at least two, at least three, at least four, at least five, at least six, at least seven, at least eight, at least nine, at least ten, or more, migration inducing factors.

Besides, it is necessary to add a photo initiator for the polymerization of free radicals induced by UV light; in this case 2-hydroxy-4'-(2-hydroxyethoxy)-2-methylpropiophenone or 2.2-dimethoxy-2-phenyl acetophenone. Different mixes and variants of these components could lead, on the one side, to regulate the hydro-gel structural properties, and to release parameters for components encapsulated in the hydro-gel. In some embodiments, the hydro-gel wall width is about 150 µM.

The controlled release may be initiate by the addition of a release factor such as, but not limited to, proteases, collagenases, or the like. Upon addition of the release factor, the factor release rate at 1 nM per $nm^2$ of wall, may be about $6 \times 10^{-11}$ $pmol/nm^2 \times h$. In some embodiments the factor release rate at 1 nM per $nm^2$ of wall, may be about $2.4 \times 10^{-7}$ $pmol/nm^2 \times h$. The release rate may be increased or decreased by about 1 fold, 2 fold, 3 fold, 4 fold, 5 fold, 6 fold, 7 fold, 8 fold. In other embodiments, the rate may be increased or decrease by about $10^1$, $10^2$, $10^3$, $10^4$, $10^5$, $10^6$.

Figure 3:
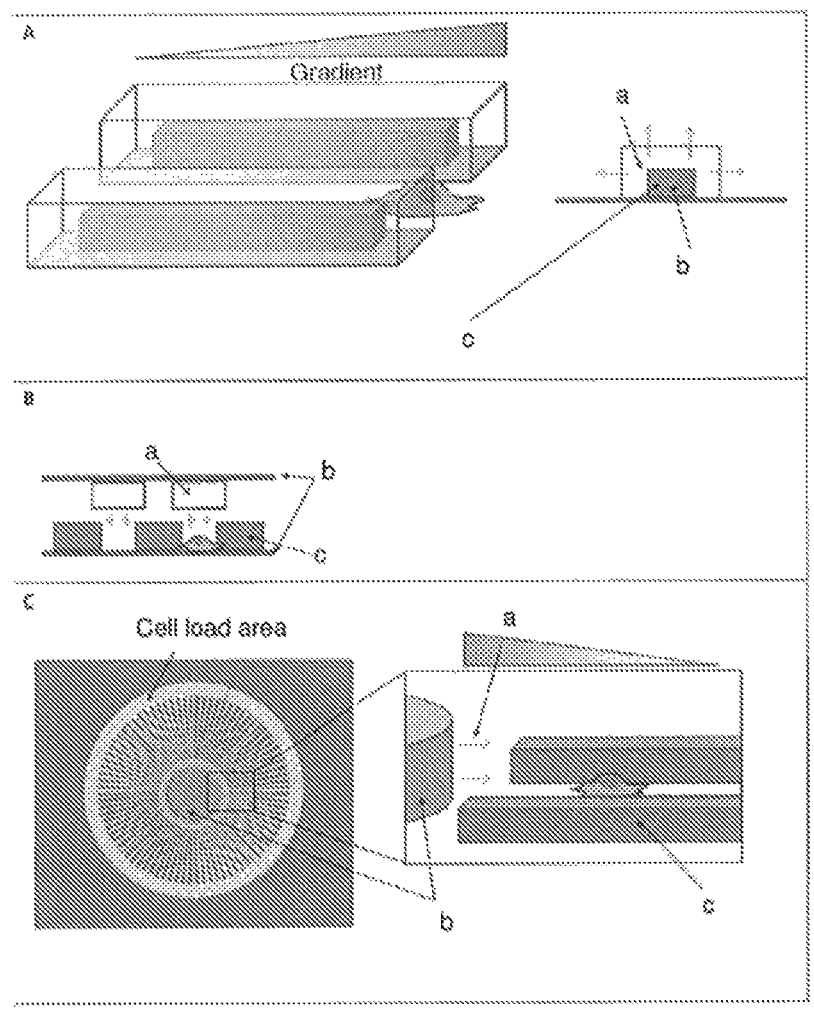
FIG. 3 includes three panels, A, B, and C, which shows the design and manufacturing alternatives related to the inclusion of a factor (encapsulated) gradient in the device. Panel A show a schematic similar to the original design, but in this case including a central element in the hydro-gel that could be another hydro-gel or material in order to increase the construct structural stability, where (a) can be hydro-gel or other material for factor controlled release, (b) can be hydro-gel or other material for structural support and (c) can be polystyrene, glass, or other material for cell migration support.

Among the device manufacturing alternatives, there is a possibility to physically separate the structural stability components and controlled release of migration inducing factors (FIG. 3). For this, two different formulation hydro-gels are generated: on the one side, the one providing stable structural support for the forming of migration lanes, which in this case is based on low molecular weight (258-700 kDa) PEGDA and, on the other hand, the second one that is part of the control element in the release of factors encapsulated in the hydro-gel. The last one is generally formed by higher molecular weight PEGDA and other monomers with load (acrylic acid and/or acrylamide), whose formula is directly related to the size nature, electrostatic properties, and the encapsulated factor hydrophobic. Alternatively, gelatin as base material for the manufacturing of hydro-gels is used to form the controlling element for the release of factors. FIG. 3 shows different inclusion alternatives in a single device for both elements.

Factors Inducing Cell Migration/Adherence:
Some migration inducing factors may comprise, but not limited to, the following:
  Thrombin (F2)
  Interleukin 8 (IL-8, CXCL8)
  Factor derivative from 1α (SDF-1α, CXCL12) cell stroma
  WNT proteins such as Wnt11 Wnt3
  Leptin (LEP)
  Interleukin-13 (IL-13)
  Angiotensin II (ANGII)
  Melanoma cell adherence molecule (MCAM, CD146)
  Interleukin 2 (IL-2)
  Fibroblast growth factors such as FGF-2 and FGF-1
  Low molecular weight hyaluronic acid (LMWHA)
  Beta transforming growth factor (TGF-beta)
  Vascular endothelial growth factor (VEGF-B and VEGF-A)
  Lysophosphatidic acid
  Regulated upon Activation, Normal T-cell Expressed, and Secreted (RANTES, CCL5)
  Interferon gamma-induced protein 10 (CXCL10, IP-10)
  Monocyte 1 chemoattractant protein 1 (MCP1, CCL2)
  Macrophage inflammatory protein 1α (MIP1α, CCL3)
  Macrophage inflammatory protein-1β (MIP-1β, CCL4)
  Chemokine (C—C motif) ligand 7 (CCL7)
  Macrophage inflammatory protein-3-beta (MIP-3-beta, CCL19)
  Chemokine (C—C motif) ligand 21 (CCL21)
  Chemokine (C—C motif) ligand 25CCL25
  Lymphocyte B chemoattractant B (CXCL13)
  Chemokine (C—X—C motif) ligand 16 (CXCL16)
  Tumor necrosis factor-α (TNF-α)
  Hepatocytes growth factor (HGF)
  Epidermal growth factor (EGF)
  Platelet derivative growth factor (PDGF)
  Insulin growth factor (IGF)
  Angiopoietin-1 (ANGPT1), and
  Granulocyte colony stimulating factor (G-CSF).

Gradient Encapsulated in Hydro-Gels

In this invention, forming of hydro-gels with an encapsulated gradient is carried out as described in FIG. 9, where continuous decreasing or discrete concentrations are included into a micro-channels circuit distributing the gradient in a series of non-polymerized and parallel hydro-gel bands. Once the flow in this circuit stops, the end of the parallel channels has a higher factor concentration, while the start has a low concentration. Later, the hydro-gel is polymerized in order to encapsulate the gradient.

The slope concentration of encapsulated factors may range from about 1 nM to 400 nM. In some embodiments, the concentrations may comprise about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 125 nM, 150 nM, 175 nM, 200 nM, 225 nM, 250 nM, 275 nM, 300 nM, 325 nM, 350 nM, 375 nM, or 400 nM.

The micro-channels circuit geometry or configuration is manufactured with "Soft-photolithography". This technique is basically the forming of a thin film of a photo-resistant material (SU-8, MicroChem MA, US) on a silicon wafer, used to manufacture microchips) and this film exposure with UV light at 365 nm wave length through a photo-mask (Microtronics, Advanced Reproductions Corporation and Photronics) only allows light to the design transparent areas. Later, this is baked at 95° C. for 15 minutes and developed using serial PGMEA washes (propylene glycol methyl ether acetate) and isopropanol (IPA). Once the silicon wafer is dry, a mix of polydimethylsiloxane (PDMS) and a organometallic catalizer is placed on the wafer and baked at 80° C. for one hour; then, the PDMS is carefully removed from the mold formed by the silicon wafer and the photo-resistant material, obtaining the negative print in the PDMS flexible elastomer (see FIG. 10 C).

This structure is placed on a polystyrene or glass plate containing a (3-trimethoxysilyl)propyl methacrylate (TM-SPMA) cover, and then the non-polymerized hydro-gel formula is loaded together with the photo-starter in order to form the gradient factor, as previously described. Once the gradient has been loaded and formed, the hydro-gel is polymerized using UV in order to encapsulate the gradient formed.

Adherence Device

The same as for the migration device, the micro-channel structure designed to create cell micro-flows and medium in the presence of factors inducing adherence, is manufactured using "Soft-photolithography" techniques. Micro-channel designs may vary, as the ones presented in FIG. 2 or FIG. 10 C.

In order to facilitate cell adherence, micro-channels may be submitted to coverage processes through the adsorption of protein components such as collagen, gelatin, fibronectin, selectin-E, or selectin-P, as well as of polysaccharides such as hyaluronic acid, cellulose, hemicellulose, and chitosan, among other. Alternative coverage generation processes involve the forming of hydro-gel layers composed of the same above mentioned components which, additionally, are capable of encapsulating cell adherence inducing factors. These inducing components may be released in a controlled way from the hydro-gels to the channels lumen, where cells will flow.

VI. Kits

Provided herein are kits comprising the following components: migration device, adherence device, incubation reagents, and developing reagents. The kits may comprise accessories including centrifuge adaptor, incubation platform, microscope adaptor, and a bubble trap fluidic low pass filter comprising a gradient fraction and mineral oil. The kit is provide with software for assessing the cell migration and adherence of a population of cells. Such software is useful for analyzing the therapeutic potential of a population of cells in a simple. The software includes algorithms for assessing cell migration, adherence, and a prediction model.

As can be appreciated from the disclosure above, the present invention has a wide variety of applications. The invention is further illustrated by the following examples, which are only illustrative and are not intended to limit the definition and scope of the invention in any way.

EXEMPLIFICATIONS

Example 1: Migration Device Designs

Some examples of the devices geometry and design may lead to different applications. One of the invention standard designs corresponds to a set of migration devices, where each migration lines group is formed by hydro-gels (e.g. formed out of salmon or bovine gelatin) or other material encapsulating different factors (FIG. 5A). The effect and contour plots of gelatin hydrogel material can be seen in FIG. 11a. FIG. 11b shows the melting characteristics of gelatin solutions (7%). In this case, the migration capacity of a particular cell sample is quantified in front of different factors. A second design includes the presence of two migration factor gradients running from the cells load area, but in the opposite direction (FIG. 5B). In this case, it is possible to explore the differential presence of cell groups contained in a heterogeneous cell sample and identify and group certain cell sub-populations according to their preferential migratory response to one or the other encapsulated factor. This last design may be extended to three, four, or more factor gradients exercising simultaneous migration induction on a single cell sample. The expansion of more factors in a same cell assay and in the same population could provide valuable information on the population heterogeneity of these cell samples (FIG. 5C).

Example 2: Exemplary Device Assay Preparation Protocol

Cells may be harvested by means known in the art. Cells are then loaded into the device by simple dropping on top of the device, and centrifuged to move cells to one end of the device which correspond to the starting position, where the concentration of factor is lower. Culture medium and activator factor release are added and the assay begins once incubating the device at 37° C. and 5% CO2 for 8-12 hr. To control for cell number, cells may be washed and stained with DAPI or any dye capable of binding nuclear DNA.

An example of the device may be seen in FIG. 12a. The device is placed on a 35 mm polysterene culture dish and consists of a cell loading wall, which will assist the positioning of cells sample at the beginning of the migration lanes after cell dropping and centrifugation, collagen-based hydrogel walls that contain the encapsulated gradient of migration-inducing factors, and migration lanes with variable width (1-50 μm) (limited laterally by the hydrogel walls and with polysterene bottom treated for cell culturing). The device comprises a series of parallel channels with an open ceiling, giving full access to the media contained in the petri dish during incubation and migration assay. Channels and the cell loading wall are fabricated with a collagen-based hydrogel, capable to encapsulated soluble factors without detectable release at storage conditions (4° C. in sterile PBS 1×).

The number of located cells at the beginning of each migration lane depends on the volume, cell size and cellular quantity of the dropped cell sample. Roughly, 40 cells/µl (cell size of 10 µm in diameter), in a total volume of 10 µl, permits the establishment of 30 to 50 cells at the beginning of each migration lane after the centrifugation step. In addition, every hydrogel wall is fabricated to contain from the starting end to the final end a linearly increasing concentration of a migration-inducing factor, in which the minimal and maximal concentration is pre-defined and controlled during the manufacturing of the device. The desired lower and higher concentration presented in the device will determine the gradient slope of encapsulated factor. In order to arrest proliferation during migration, after localizing the cells at the beginning of the migration lanes, the device may be incubated with the appropriated free FBS medium for the specific cells. The medium is supplemented with a factor release activator, initiating the controlled delivery of the encapsulated factors from the hydrogel into the migration lanes. Moving cells along the migration lanes start sensing increasing amount of release factors as they start getting closer to the final end of the migration lanes. The increasing concentration directs the cell migration.

Controlled Release of Encapsulated Factors

Before starting the migration assay, the added release activator (e.g., a protease, such as collagenase) triggers the delivery of encapsulated factors (e.g., VEGF) into the migration lanes, forming a linear concentration gradient of factor along the channels (FIG. 12b). Cells sense the increasing concentration of factor, directing their migration toward higher concentration. Rate of factor release is controlled by the concentration of release activator supplemented in the culture media. Activator is a biologically cell inert reagent that creates a stable gradient along the open migration channels. Very low quantity of the activator is enough to induced directed cell migration due to the close proximity of the cells from the source of released factor, the hydrogel wall. Release activator basically degrades the polymerized hydrogel-forming material and the encapsulated migration factor within the hydrogel is controllable release during slow degradation.

Collagenase is shown to greatly increase the release of VEGF from degradation of the hydro-gel, in some instances as much as 40% (FIG. 14). VEGF degradation by percent is shown in FIG. 15. FIG. 16 shows a 12 hour scratch test assay using bone marrow mesenchymal stem cells (BM MSCs) with and without collagenase, suggesting collagenase facilitates cell migration. The device may be stored under a variety of conditions. The device can be maintained at 4° C. in sterile PBS 1×. Alternatively, the device can be maintained at −20° C. in cryopreserved media. After long-term storage the device requires an overnight washing step in PBS 1× to remove the cryopreservant before the migration assay. Maintenance of bioactivity of encapsulated factors is tested using the activity assays pre-established by the particular factor suppliers. Additionally, the device may be sterilized by gamma irradiation. A summary table of technical characteristics in an exemplary device can be seen in Table 1 below.

TABLE 1

| Technical Characteristics | |
|---|---|
| Technical Characteristics | |
| Geometry design | |
| Number of migration Channels | 15 |
| Channel width | 1-50 µm |
| Channel height | 50 µm |
| Hydrogel wall width | 150 µm |
| Channel length | 10 mm |
| Formulation | |
| Hydrogel wall | Collagen-based modified composite |
| Encapsulated factor | Any water soluble factor |
| Slope of encapsulated factor | Usually from 1 nM to 400 nM |
| Factor release rate at 1 nM per nm² of wall | $6 \times 10^{-11}$ pmol/nm² × h |
| Factor release rate at 400 nM per nm² of wall | $2.4 \times 10^{-7}$ pmol/nm² × h |
| Storage Conditions | |
| Maintain at 4° C. in sterile PBS 1X | 6 months |
| Maintain at −20° C. in cryopreserved media | 3 years |
| Protocol | |
| Centrifuge | Swing rotor centrifuge |
| Centrifugation | up to 500 xg |
| Cell attachment incubation | 1-3 h |
| Cell adhesion coating | Any suitable por polysterene cell culture dishes |
| Time for migration assay | 8-12 h |
| Cell visualization | fluorescent microscope (DAPI staining)/bright-field microscope (Violet crystal) |
| Imaging | 4X or 10X objective recomended |

Example 3: Exemplary Migration Assay Protocol

Cell Loading

Harvest cells and re-suspend them to obtain a concentration of 4×10⁵ cell/mL. Place the centrifuge adaptor inside the biosafety cabinet (see FIG. 13a). Place the device on the centrifuge adaptor, remove the storage buffer from the device and remove the buffer including that which remains at the loading wall (see FIG. 13a). Place the (device without the lid) on the centrifuge adaptor to obtain a 60 degree inclination, and the interior of the open petridish plate pointing to the left or right. Load 10 µL of the cell solution obtained previously. The loading must be done precisely and well distributed all across the loading wall, as shown in the FIG. 13b.

Close the device with petridish lid, cap the centrifuge adaptor using its respective lid and spin the cells for 5 min at 180×g. Open the adaptor, open the device and remove any liquid that might be present at the end of the device (see FIG. 13c) and add 15 µL of culture medium as shown in FIG. 13b. Place the device on the incubator for 45-60 min. To maintain the inclination over the incubation time, use the incubator (see FIG. 13d). After incubation for cell attachment, wash the device with 2 mL of PBS as shown (see FIG. 13e). Check that all cells are adhered at the starting point. Proceed to add 2 mL of proper culture medium and activator factor release and let the assay begin incubating at 37° C. and 5% CO2 for 8-12 hr. (see FIG. 13e).

Cell Staining and Results

Proceed to remove the media and wash with 2 mL of PBS. Remove the PBS and add 50 µL of DAPI Fluorescent reagent over the device only as shown in FIG. 13f and incubate at room temperature for 10 minutes. Wash 2 times with 2 mL of PBS. Add 2 mL of PBS and take pictures using a 4× or 10× objective of the device as shown in FIG. 13g.

Example 4: Formation of a Linear Gradient

In order to generate a microfluidic system capable to fill a series of parallel channels with a linear gradient of defined factors, the "fluidic low pass filter" was created. Input flow tubing contains a series of fractions at decreasing or ascending factor concentration separated by a volume of a hydrophobic a less dense solution, such as mineral oil. The low pass filter is a broader cylindrical chamber capable of removing the mineral oil by accumulation the oil drops at the upper part of the filter, which is driven by the lower density of the oil. This oil removal will allow the different fractions to join, and depending on the flow speed and the diameter of the low pass filter, concentration diffusion will be generated between the adjacent fractions before entering the parallel channels. This will turn a stepwise concentration gradient into a continuous linear gradient in the parallel channels. A schematic of gradient formation can be found in FIG. 17.

Example 5: Fluidic Low Pass Filter Simulation

Once the gradient has been injected into the parallel microfluidic channels, having one end of the gradient at the beginning of the channels and the other end at the final section of the channels, the hydrogel is polymerized through an induction using UV light. This will sequestrate or encapsulate the gradient of factor inside the polymerized hydrogel. After polymerization, the PDMS negative mold can be removed and the device would be ready for use after washing, sterilization step and activation using the activator reagent. Concentration gradient at the parallel channels using different diameters of the low pass filter can be seen in the simulation shown in the FIG. 18.

Example 6: Subpopulation Sorting Validation

Cells were FACS sorted to test whether the device in fact distinguish cells according to cell subpopulation with different migration capacity. Assay results show cells were sorted by subpopulation according to the presence or absence of the surface cell marker CD56 (FIG. 19). Digital photographs showing cell migration in a scratch assay and in the migration device can be seen in FIG. 20, and a graphical representation showing migration patterns for subpopulations of cells obtained from the migration device can be seen in FIG. 21.

Example 7: Model of Device Application, Validation, and Operation

In a pre-clinic animal model of chronic kidney damage, where a 5/6 nephrectomy was performed on 8-week old rats (180 g approximately) (literature: "Drug Discov Today Dis Models. 2010; 7 (1-2): 13-19) Models of Chronic Kidney Disease), treatments after 1 day post-nephrectomy with $1\times10^6$ intravenous injection of mesenchymal cells from different cells samples, present varied functional recovery levels measured, such as the protein amount in urine collected within a 24-hour range (proteinuria). Due to the fact that this is a standardized model, the tissue functional recovery level depends on the cells therapeutic quality in the injection model. In rats not treated with mesenchymal stem cells, the proteinuria increase or increasing line progression is 4.5 mg per day, reaching total levels of around 400 mg after 84 days (total collection of protein excreted through urine in 24 hours). In the case of animal models with chronic kidney damage and mesenchymal stem cells treatment, decrease in the proteinuria levels progression is observed in a 0.7 mg to 3.5 mg range per day. As from the 70th day, in some cases proteinuria levels observed were in open regression, with declines of up to −3 mg a day.

Mesenchymal stem cells were isolated from menstrual tissue of women of different ages and Umbilical cord mesenchymal cells were isolated from different patients as well. Different experimental groups may be described as follows: limited growth or multiplication against highly extended multiplication, varied conditions or partial oxygen stress (normoxia and hypoxia), thawing and immediate injection, and thawing, conditioning, and injection. An experimental migration data set regarding different factors and tissue recovery, measured from proteinuria data, was obtained from each cell sample submitted to different treatments. Recovery degree corresponds to the variable response in the data set, linearly quantified, where 100% of recovery includes 0.7 mg per day progression rising line (calculated after 70 days from the inoculation with mesenchymal stem cells) and 0% correspond to a progression rising line equal to negative controls (4.5 mg per day). In order to quantify cell migration or adherence in front of each factor in the devices, image analyses were performed using computer display programs and an average Xi behavior vector was calculated. Based on each sample and considering different samples from cell groups with different treatments, the following data were obtained:

(Y, Xa, Xb, Xc, Xd, Xe, Xf, Xg)
Y=Therapeutic potency (measured in percentages)
Xi=Migration vector of 100 cells exposed to factor i (measured in m−7)

A matrix was built formed by this data in order to create a therapeutic potential predictive model using the step by step regression methodology (Stepwise regression). Inducing factors used in the first instance were IL-8, IL-2, SDF-1α, CXCL10, CCL2, TGF-beta, LMWHA, and CCL7. Later, the predictive model obtained, with a correlation value higher than 0.98, isolated SDF-1α, CXCL10, TGF-beta, and CCL2 as predictive factors for the recovery of proteinuria levels in a chronic kidney damage model, presented the following beta standardized coefficient values, respectively: 0.744, 0.077, 0.232, and 0.062. In the case of values obtained with the cell adherence device, correlation values, factor identities, and their coefficients are not far from that obtained with the migration kit. The device and the statistics model obtained in this pre-clinical assay could be used as a kit for therapeutic quality control in the different production stages of a cell product production and injection to patients (recruiting, expansion, production batch to the market, and quality test prior to injecting the patient); however, its validity is proven in the case of this animal model. Therefore, it is necessary to verify the model validity in clinical assays and, if necessary, modify and adjust the model for cases with human patients using real clinical data.

INCORPORATION BY REFERENCE

The contents of all references, patent applications, patents, and published patent applications, as well as the Figures and the Sequence Listing, cited throughout this application are hereby incorporated by reference in their entirety as if each individual publication or patent was specifically and individually incorporated by reference. In case of conflict, the present application, including any definitions herein, may control.

EQUIVALENTS

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention may become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A device adapted to assess cell migration responses of a population of cells, the device comprising:
    a) a cell load chamber;
    b) at least two migration assay lanes or lines formed by two parallel hydrogel side bands and allowing migration, wherein the migration assay lanes or lines are parallel, wherein a migration area in each assay lane is delimited in a lower part by the two side bands and material capable of supporting the two side bands and allowing migration, wherein the assay lanes or lines are open in an upper part and the migration is produced on the material; and
    c) wherein the hydrogel comprises an encapsulated migration inducing factor.

2. The device according to claim 1, wherein the assay lines or lanes have a width of about 150 μm.

3. The device according to claim 1, wherein the assay lanes or lines are spaced at a distance apart to form at least one assay channel.

4. The device according to claim 1, wherein the assay channel has a width of about 50 μm, the assay channel has a height of about 50 μm and the assay channel has a length of about 10 mm.

5. The device according to claim 1, wherein the encapsulated factor gradient comprises a concentration range of migration inducing factor from about 1 nM to 400 nM.

6. The device according to claim 5, wherein the migration or adherence inducing factor is selected from the group consisting of Thrombin (F2), Interleukin 8 (IL-8, CXCL8), Factor derivative from 1α (SDF-1α, CXCL12) cell stroma, Wnt11, Wnt3, Leptin (LEP), Interleukin-13 (IL-13), Angiotensin II (ANGII), Melanoma cell adherence molecule (MCAM, CD146), Interleukin 2 (IL-2), Fibroblast growth factor 1 (FGF-1), Fibroblast growth factor 2 (FGF-2), Low molecular weight hyaluronic acid (LMWHA), Beta transforming growth factor (TGF-beta), Vascular endothelial growth factor (VEGF-B and VEGF-A), Lysophosphatidic acid, Regulated upon Activation, Normal T-cell Expressed, and Secreted (RANTES, CCL5), Interferon gamma-induced protein 10 (CXCL10, IP-10), Monocyte 1 chemoattractant protein 1 (MCP1, CCL2), Macrophage inflammatory protein 1α (MIP1α, CCL3), Macrophage inflammatory protein-1β (MIP-1β, CCL4), Chemokine (C—C motif) ligand 7 (CCL7), Macrophage inflammatory protein-3-beta (MIP-3-beta, CCL19), Chemokine (C—C motif) ligand 21 (CCL21), Chemokine (C—C motif) ligand 25CCL25, Lymphocyte B chemoattractant B (CXCL13), Chemokine (C—X—C motif) ligand 16 (CXCL16), Tumor necrosis factor-α (TNF-α), Hepatocytes growth factor (HGF), Epidermal growth factor (EGF), Platelet derivative growth factor (PDGF), Insulin growth factor (IGF), Angiopoietin-1 (ANGPT1), and Granulocyte colony stimulating factor (G-CSF), or combinations thereof.

7. The device according to claim 1, wherein the encapsulating factor gradient is released upon addition of a release factor.

8. The device according to claim 7, wherein the release factor is a protease.

9. The device according to claim 8, wherein the protease is a collagenase.

10. The device according to claim 1, wherein the device is adapted to assess cell migration response of a population of cells selected from the group consisting of mesenchymal stem cells, early mesenchymal/stromal precursor cells, adipose tissue-derived stem cells, Muse-AT cells, hematopoietic cells, hematopoietic stem cells, platelets, Kupffer cells, osteoclasts, megakaryocytes, granulocytes, NK cells, endothelial precursor or progenitor cells, pluripotent cells, CD34+ cells, Stro-1+ cells, Stro-3+ cells, CD29+ cells, CD166+ cells, Thy-1+ or CD90+ stem cells, CD44+ cells, immune cells, monocytes, leukocytes, lymphocytes, Band T cells, NK cells, macrophages, neutrophil leukocytes, neutrophils, neutrophil granulocytes, adult and embryo stem cells, endoderm mesenchymal stem cells (MSCs), mesoderm MSC, ectoderm MSC, early mesenchymal/stromal precursor, adipose tissue-derived stromal/stem cells, multipotent stem cells, adipocytes, osteocytes, chondrocytes, myoblasts, cardiomiocytes, astrocytes, and neuronal/glial cell lineages.

11. The device according to claim 1, wherein the hydrogel comprises gelatin, hyaluronic acid, alginate, agarose, chitose, gellan gum, collagen, collagen based hydrogel, high methacrylated salmon gelatin at 10%, polyethylene glycol, polyethylene acid, polyvynylpirrolidone, polyacrylamide, polymetyl methacrylate, polyethylene glycol dyacrilate based formula (PEGDA), pentaerythritol triacrylate (PETA), acrylic acid, acrylamide, or combinations thereof.

12. The device according to claim 11, wherein the hydrogel comprises collagen based hydrogel.

13. The device according to claim 1, wherein the hydrogel further comprises a photo initiator comprising 2-hydroxy-4'-(2-hydroxyethoxy)-2-methylpropiophenone or 2,2-dimethoxy-2-phenyl acetophenone.

14. The device according to claim 1, which is adapted to assess cell adherence response of a population of cells, the device comprising:
    a) a micro-channel circuit for perfusion of a liquid medium;
    b) an internal substrate limiting channel edges;
    c) at least one entry for a liquid medium injection; and
    d) at least one entry for sample cells.

15. A method to quantify cell migration response of a population of cells, the method comprising the steps of:
    providing the cells to the device according to claim 1;
    incubating the cells under conditions to facilitate migration;
    calculating migration distance of cells contained in a sample to generate at least one score;
    incorporating the at least one score in a statistical mathematical model specific to a cell type and pathology;
    obtaining a correlation between the factor defined and therapeutic quality level; and calculating a general performance value and therapeutic quality of the cell sample.

16. A method of using the device according to claim 1, comprising assessing therapeutic characteristics of a sample stored in a cell bank.

17. A method of using the device according to claim 1, comprising performing quality control with the device before therapy and after thawing a cell sample.

18. A method of using the device according to claim 1, comprising assessing cell migration in presence of factors related to a rate of success in different treatments.

19. A method of using the device according to claim 1, comprising calculating therapeutic variability of a cell sample or product according to cell's activity in the device.

20. A method of using the device according to claim 1, comprising calculating cell doses to be administered to a patient during treatment.

21. A method of using the device according to claim 1, comprising assessing cell migration in presence of factors related to a rate of success in kidney damage recovery.

* * * * *